United States Patent
Schenberger et al.

(10) Patent No.: US 7,691,106 B2
(45) Date of Patent: Apr. 6, 2010

(54) TRANSVERSE ACTING SURGICAL SAW BLADE

(75) Inventors: Jon C. Schenberger, Placerville, CA (US); Michael G. Fisher, Folsom, CA (US)

(73) Assignee: Synvasive Technology, Inc., El Dorado Hills, CA (US)

( * ) Notice: Subject to any disclaimer, the term of this patent is extended or adjusted under 35 U.S.C. 154(b) by 857 days.

(21) Appl. No.: 11/234,754

(22) Filed: Sep. 23, 2005

(65) Prior Publication Data

US 2007/0083209 A1    Apr. 12, 2007

(51) Int. Cl.
*A61B 17/14* (2006.01)

(52) U.S. Cl. .................................... 606/82

(58) Field of Classification Search .............. 606/79, 606/82, 176, 177; 30/182, 209, 214, 392
See application file for complete search history.

(56) References Cited

U.S. PATENT DOCUMENTS

| | | | |
|---|---|---|---|
| 1,179,910 A | 4/1916 | Greenfield | |
| 1,201,467 A | 10/1916 | Hoglund | |
| 1,726,241 A | 8/1929 | Schubert | |
| 2,702,550 A | 2/1955 | Rowe | |
| 2,854,981 A | 10/1958 | Morrison | |
| 3,554,197 A * | 1/1971 | Dobbie | 606/178 |
| 3,678,934 A | 7/1972 | Warfield et al. | |
| 3,978,862 A | 9/1976 | Morrison | |
| 4,513,742 A * | 4/1985 | Arnegger | 606/178 |
| 4,567,798 A | 2/1986 | Brdicko | |
| 4,584,999 A | 4/1986 | Arnegger | |
| 4,617,930 A | 10/1986 | Saunders | |
| 4,768,504 A | 9/1988 | Ender | |
| 5,087,261 A | 2/1992 | Ryd et al. | |
| 5,092,869 A * | 3/1992 | Waldron | 606/82 |
| 5,122,142 A | 6/1992 | Pascaloff | |
| 5,178,626 A | 1/1993 | Pappas | |
| 5,201,749 A | 4/1993 | Sachse et al. | |

(Continued)

OTHER PUBLICATIONS

International Preliminary Report on Patentability of PCT Application No. PCT/US2006/037014, issued Mar. 26, 2008, 8 pages total.

(Continued)

*Primary Examiner*—Eduardo C Robert
*Assistant Examiner*—Elana B Fisher
(74) *Attorney, Agent, or Firm*—Townsend and Townsend and Crew LLP

(57) ABSTRACT

Various embodiments provide surgical cutting devices and systems for orthopedic and other procedures. Specific embodiments provide saw devices for accessing and cutting subjacent bone and other tissue while minimizing injury to surrounding tissue. One embodiment provides a transverse acting saw blade for performing surgical cuts to bone tissue with minimal injury to surrounding tissue. The blade comprises an elongated member having a first portion and a second portion and a longitudinal and lateral axis. The first portion is configured to engage a drive source to produce longitudinal movement of the first portion that is atraumatic to surrounding tissue. The second portion includes a cutting surface. The longitudinal movement of the first portion is converted to a lateral movement of the second portion that is sufficient to cut engaged bone tissue with the cutting surface. The movement of the second portion is substantially transverse to the movement of the first portion.

26 Claims, 20 Drawing Sheets

U.S. PATENT DOCUMENTS

| | | |
|---|---|---|
| 5,263,972 A | 11/1993 | Evans et al. |
| 5,306,285 A | 4/1994 | Miller et al. |
| 5,382,249 A | 1/1995 | Fletcher et al. |
| 5,403,318 A | 4/1995 | Boehringer et al. |
| 5,409,491 A | 4/1995 | Boehringer et al. |
| 5,439,472 A | 8/1995 | Evans et al. |
| 5,496,325 A | 3/1996 | McLees |
| 5,507,763 A | 4/1996 | Petersen et al. |
| 5,554,165 A | 9/1996 | Rait et al. |
| 5,569,257 A | 10/1996 | Arnegger |
| 5,735,866 A * | 4/1998 | Adams et al. ............... 606/178 |
| 5,839,196 A | 11/1998 | Trott |
| 5,846,244 A | 12/1998 | Cripe |
| 6,022,353 A | 2/2000 | Fletcher et al. |
| 6,113,618 A * | 9/2000 | Nic ........................... 606/176 |
| 6,503,253 B1 | 1/2003 | Fletcher et al. |
| 6,514,259 B2 | 2/2003 | Picard et al. |
| 6,656,186 B2 | 12/2003 | Meckel |
| 6,723,101 B2 | 4/2004 | Fletcher et al. |
| 6,875,222 B2 | 4/2005 | Long et al. |
| 6,896,679 B2 | 5/2005 | Danger et al. |
| 7,497,860 B2 | 3/2009 | Carusillo et al. |
| 7,527,628 B2 | 5/2009 | Fletcher et al. |
| 2002/0116022 A1 | 8/2002 | Lebouitz et al. |
| 2003/0014067 A1 | 1/2003 | Kullmer et al. |
| 2003/0075162 A1 | 4/2003 | Hamilton |
| 2004/0243136 A1 | 12/2004 | Gupta et al. |
| 2005/0065530 A1 | 3/2005 | Stauch et al. |
| 2005/0113840 A1 * | 5/2005 | Metzger et al. ............... 606/88 |
| 2008/0027449 A1 | 1/2008 | Gundlapalli et al. |
| 2008/0243125 A1 | 10/2008 | Guzman et al. |
| 2009/0093814 A1 | 4/2009 | Fletcher et al. |
| 2009/0093815 A1 | 4/2009 | Fletcher et al. |

OTHER PUBLICATIONS

Stryker® Precision Oscillating Tip Saw—Ref 6209, Instruction for Use, Sep. 2006, 21 pages total.

Stryker Precision™ Oscillating Tip Saw [pamphlet], 2006, 2 pages total.

* cited by examiner

TRANSVERSE ACTING SURGICAL SAW BLADE

BACKGROUND OF THE INVENTION

Field of the Invention

Embodiments of the invention relate to surgical saws. More specifically, embodiments of the invention relate to surgical saw blades having a mechanical motion configured to minimize trauma to surrounding tissue not engaged by the blade.

Surgical saws of the sagittal type for performing bone surgery have been extensively utilized for many years. These saws have normally employed an elongated saw blade having a toothed segment on one end thereof, with the other end of the blade being pivotally mounted to permit angular oscillation of the blade. Typical surgical saws do not permit deep-reach cutting, without contacting and possibly damaging adjacent tissue since deep cuts require that the toothed edge of the blade be spaced a greater distance from the pivot axis, thereby resulting in larger peripheral movement which often causes damage to the tissue surrounding the bone. In particular they do not provide an atraumatic means of transmitting motion to the cutting portion of the blade. Additionally, smaller surgical incisions as popularized by less-invasive surgical techniques reduce the width-to-length ratio, increasing the possibility of damaging adjacent tissue.

While some devices have attempted to use various mechanisms gears, belts, pulleys or linkage rods etc. to transmit motion to a cutting portion of the blade without having one long moveable blade connected to a drive source, these devices have the drawback of having complicated mechanisms which can be difficult and costly to assemble.

Accordingly, there is a need for a surgical saw and saw blade which can be threaded through surgical access incisions, fed down to tissue or bone requiring cutting or resection, and make the cut or perform the resection without injuring or endangering the surrounding bone or tissue. There is also a need for a surgical saw and saw blade which can be utilized for deep cuts while maintaining minimal, atraumatic motion of the longitudinal sides of the saw blade, and transverse motion of the toothed end of saw blade, allowing effective cutting and or resection of tissue or bone.

BRIEF SUMMARY OF THE INVENTION

Various embodiments provide surgical cutting devices and apparatus for orthopedic and other surgical procedures. Specific embodiments provide saw devices for accessing and cutting subjacent bone and other tissue while minimizing injury to surrounding tissue. One embodiment provides a transverse acting saw blade for performing surgical cuts to bone tissue with minimal injury to surrounding tissue. The blade comprises an elongated member having a first portion and a second portion and a longitudinal and lateral axis. The first portion is engageable with a drive source to produce longitudinal movement of the first portion that is atraumatic to surrounding tissue. The second portion includes a cutting surface. The longitudinal movement of the first portion is converted to a lateral movement of the second portion that is sufficient to cut engaged bone tissue with the cutting surface. The movement of the second portion is substantially transverse to the movement of the first portion. As will be described herein, the motion of the cutting portion is achieved through the structural design of the blade body itself vs. the use of gears, belts, chains, linkage rods, etc. This allows for low cost and ease of manufacturability of the blade.

The elongated member can include a motion converter configured to convert longitudinal displacement of the first portion to a lateral displacement of the second portion. In preferred embodiments the motion converter comprises an opening disposed on the elongate member which can include a first opening and second opening. The first opening has a shape configured to bias the first portion toward longitudinal movement when engaged by the drive source and the second opening has a shape configured to convert a longitudinal displacement of the first portion to a lateral displacement of the second portion. In a preferred embodiment the first opening is slot shaped and the second opening has at least a partially rounded shape and can comprise a plurality of openings. Also at least one of the first and second portions or the motion converter can have differing chemical composition, mechanical properties, and geometrical shapes, including three-dimensional shapes, such as surface contours designed to enhance the motion conversion. These differing properties can be produced by annealing or tempering selected portions of the blade using laser, induction heat, or other methods. Three dimensional shapes including surface contours can be chemically-milled, cast, forged, cold-formed, laser-milled, electronic-discharged machined, conventionally machined or molded into the motion converter.

The drive source can be positioned on the saw device and can be a mechanical, electrical, hydraulic or pneumatic drive. In a preferred embodiment, the drive source is a rotary drive source including a cam which engages the blade to effect reciprocal motion of the first portion of the elongated member. In many embodiments, the blade can include a sleeve disposed over at least a portion of the elongated member. The sleeve is configured to laterally support the blade during cutting, while the sleeve itself remains stationary. The sleeve can also be configured to fit tightly in or on various cutting guides without causing high-speed friction on or in the cutting guide. The sleeve can have lumen configured to provide irrigation of the blade or target tissue site. The sleeve can comprise polymer or other material and can also include a lubricous coating on an inner lumen wall.

Another embodiment provides a surgical saw system for performing surgical cuts to bone tissue with minimal injury to surrounding tissue. The system comprises an embodiment of the saw blade described above and a surgical saw configured to use the blade. The saw device is typically a reciprocating saw and can be hand held. The device can include one or more conduits or connections to provide power to the drive source as well as connections for irrigation/aspiration and connections for electrical coupling to the blade or to sensors positioned on the blade. The system can also comprise a cutting guide configured to be used with the blade and the saw device.

An exemplary method of using an embodiment of the transverse acting blade the surgeon can make a small usually linear incision above the target tissue bone, for example the femur. The distal portion of the saw blade is then inserted through the incision either directly or through a port or cutting guide. Then by visual guidance, by feel, or image guidance (e.g., infrared, radio, electromagnetic, ultrasonic, arthroscopic or other viewing means) the distal portion of the blade is advanced until the target tissue bone is reached. Surrounding tissue, such as bone or fascia, can be pushed aside or partially retracted. The drive source is then activated and cutting begins. The cutting can also be done under image guidance, by direct viewing of the surgical site, by feel or a combination thereof. The surgeon can make a continuous cut without the need to stop due to the risk of injuring adjacent tissue. Longer cuts can be made by angling the proximal portion of the blade side to side through the incision site such that distal end moves through a desired cutting length. During this process, the lateral motion of the non-cutting section of the blade remains negligible such that non cutting portion is tissue atruamatic. Depending upon the blade, the applied force and blade speed can be monitored to stay within desired ranges. Also irrigation and aspiration can be used at the surgeon's discretion. Depending upon the embodiment, irrigating fluid can be supplied through a channel in the blade or externally. Upon completion of the cut, the blade is removed. These and other embodiments and aspects of the invention are described in further detail below.

BRIEF DESCRIPTION OF THE DRAWINGS

FIG. 1b is a perspective view of the distal portion of the embodiment of FIG. 1a.

FIG. 2b is a perspective view of the distal portion of the embodiment of FIG. 2a.

FIG. 3b is a lateral view illustrating transverse action of the blade of embodiment 3a.

DETAILED DESCRIPTION OF THE INVENTION

Figure 1:
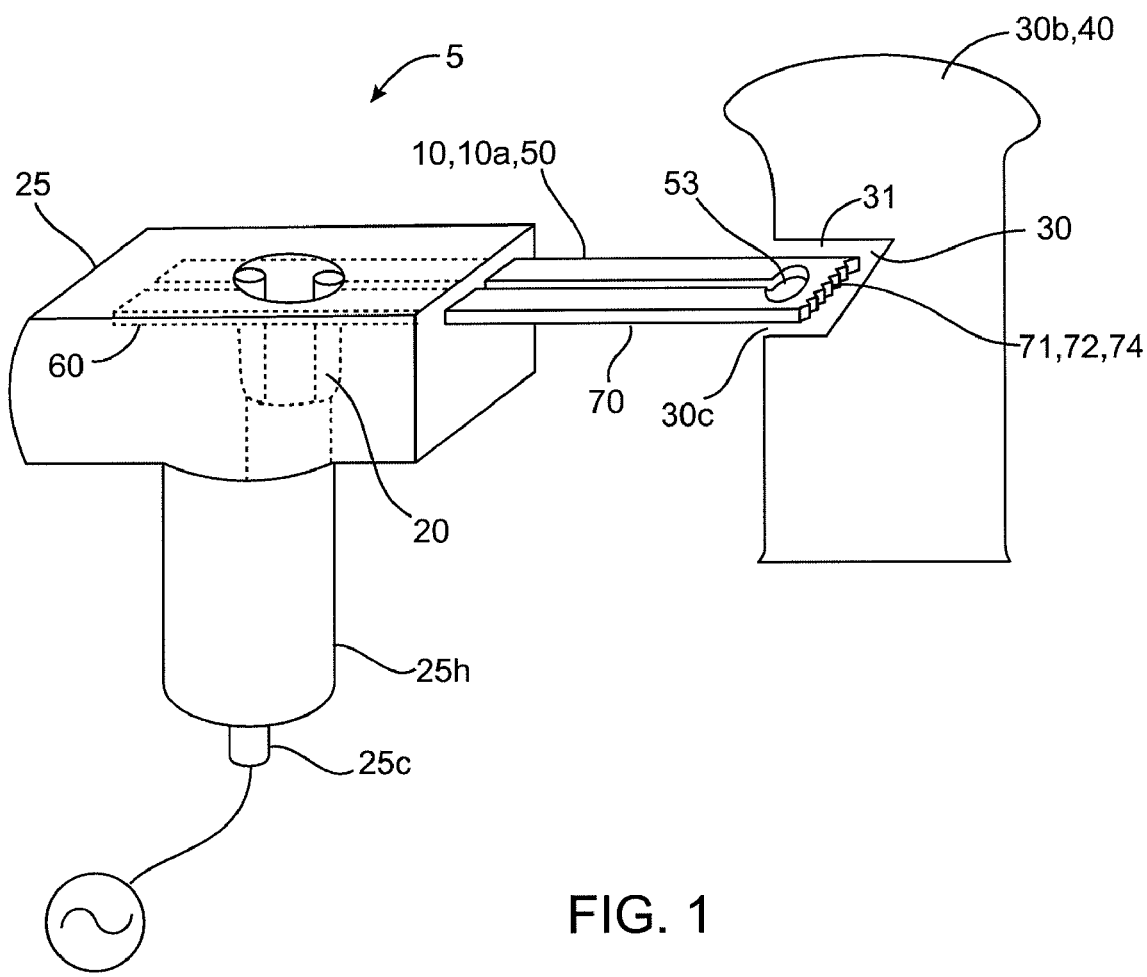
FIG. 1 is a lateral view of an embodiment of a surgical cutting system having a transverse acting blade.

Referring now to FIGS. 1-5, in various embodiments a saw blade system 5 can include a saw blade 10 configured to be engaged by a drive source 20 to cut a target tissue site 30 (or cutting site) of bone 30b or other tissue 40. In many embodiments, blade 10 comprises an elongated member 50 having a lateral axis 51 and longitudinal axis 52. Elongated member 50 includes a proximal portion 60 and distal portion 70. Proximal portion 60 includes a proximal end 61 and an engagement section 62 configured to movably engage drive source 20. Distal portion 70 includes a distal end 71 a cutting section 72 which can comprise a plurality of teeth 74 which make a cut or kerf 31 at the tissue site. Drive source 20 can be incorporated into a saw device 25 described herein.

Figure 3A:
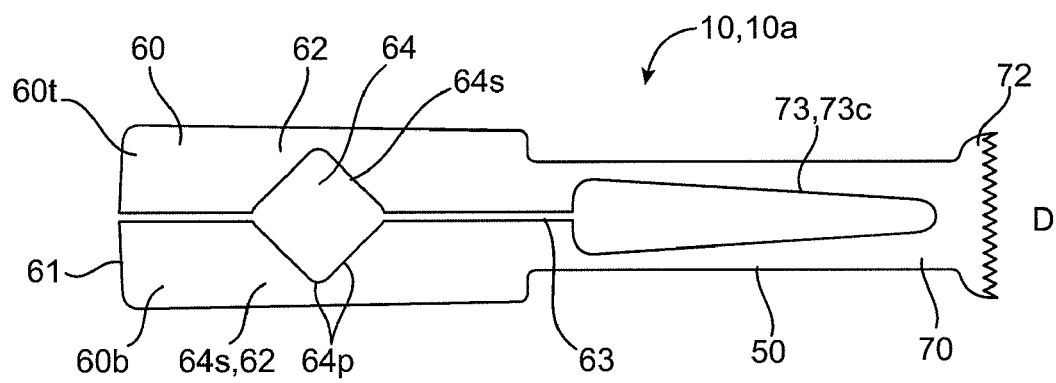
FIG. 3a is a lateral view of another embodiment of the saw blade.
Figure 3B:
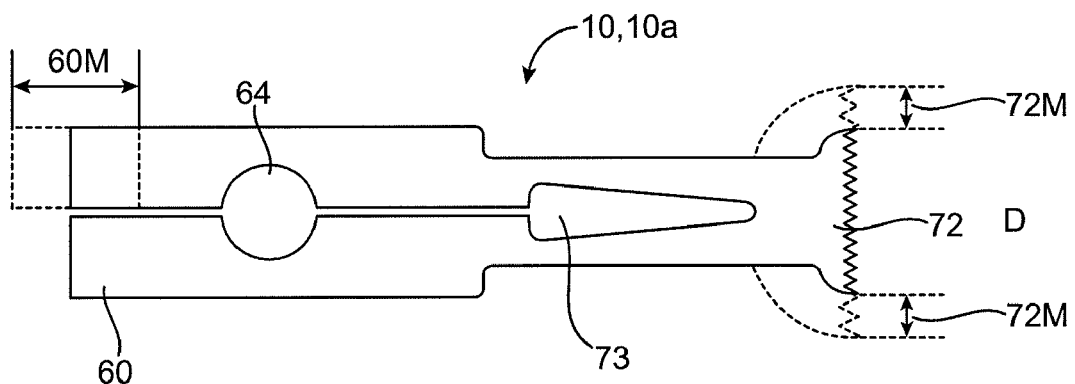

In many embodiments, the blade can include one or more openings or spaces 53 which can positioned on one or both of proximal and distal portions 60 and 70. Opening 53 is sized and shaped to convert or translate movement of the proximal portion in one direction (typically longitudinal) into movement of the cutting section 72 in another direction (typically lateral). Also opening 53 serves to convert reciprocal movement of proximal portion 60 into a oscillatory movement of cutting section 72. Further, as discussed below, opening 53 can be configured to direct the movement of the proximal and distal portions when the blade is engaged by the drive source so that that blade is a transverse acting blade 10a. That is the cutting motion of blade at cutting section 72 is substantially transverse to the motion of proximal portion 60 induced by drive source 20 as is shown in FIG. 3b. Also as discussed herein, opening 53 can also define top and bottom portions of the blade such as top and bottom portions of the proximal portion 60 of the blade.

One or more openings 53 can also be configured for debris collection, aspiration or irrigation, or access of a viewing device. In alternative embodiments, additional openings can be used for debris collection and/or irrigation, aspiration or access of a viewing device (e.g., a fiber optic view device) In such embodiments, the opening can comprise a channel running along all or a portion of the blade. Typically, such channels will run along a longitudinal axis of the blade, but they can also be laterally or otherwise oriented. In one embodiment one opening can be used for aspiration, one for irrigation and another for a viewing device. The openings can be configured to allow for continuous or near continuous aspiration/irrigation or viewing with the viewing device. In use, this allows the surgeon to continue with cutting procedure without the need to stop for one or more of aspiration, irrigation or viewing of the tissue site since he can be continuously be performing these operations during the cutting procedure.

A discussion will now be presented of the configuration of the proximal and distal portions of the blade. In many embodiments, at least a portion of blade 10 is configured to be inserted through an incision site 30i to cut underlying target bone at target tissue site 30. Accordingly, blade 10 including proximal portion 60 will typically have a substantially straight shape so as to access and cut tissue directing beneath the proximal portion. However in alternative embodiments (not shown), the proximal portion can 60 have a curved, right angle or even a U shape so as to access tissue that is offset from or otherwise not directly underneath the incision site. In use, such embodiments allow the surgeon to cut target bone or other tissue that is obstructed by other anatomical structures such as bone, organs, vasculature and nerves. For example, in one embodiment a blade having a right angle shaped proximal portion could be used to cut tissue that is within a cavity or recess of other tissue. Similarly, embodiments of the proximal member having a curved shape can be used to maneuver around curved tissue structures such as organs or blood vessels to reach a target site without cutting them. Also in many embodiments, proximal portion 60 can have a tapered section 60T. The non tapered or wider portion of proximal portion 60 can be configured for engagement with a reciprocating drive source while the tapered section has a smaller width allowing easier access to a selected tissue site.

In many embodiments, proximal portion 60 includes a longitudinal slot 63 extending along the length of the proximal section and defining top and bottom proximal portions 60*t* and 60*b*. Typically, slot 63 will be positioned on a longitudinal center line 52*c* so as to bisect the proximal portion into equal top and bottom portions. Alternatively, slot 63 can be positioned off-center line 52*c*. Also slot 63 will typically be continuous with an opening 73 in distal portion 70 so as to form opening 53. In such embodiments, slot 63 can also be used for purposes of irrigation or aspiration of the tissue site. Alternatively slot 63 can be discontinuous from opening 73.

Engagement section 62 can comprise any portion of proximal portion 60. In many embodiments, engagement section 62 comprises an opening 64 as is shown in the embodiment of FIG. 3*a*. Typically, opening 64 will be continuous with slot 63 such that when drive source 20 engages opening 64 it produces longitudinal motion of top portions 60*t* (or bottom portion 60*b*) along slot 63 which is converted to lateral motion at the distal portion of the blade 70 as is shown in FIG. 3*b*. In these and related embodiments, the surface 64*s* of opening 64 can be configured to function as a cam follower. The profile 64*p* of surface 64*s* can be configured to control the amount of longitudinal movement 60*m* of proximal portion 60 and thus in turn the amounts of lateral movement of 72M of cutting section 72. In a similar respect profile 64*p* can be used to control the speed of the cutting section 72. In various embodiments, profile 64*p* can be diamond shaped, circular, oval, parabolic, hyperbolic or other curved profile. In a preferred embodiment profile 64*p* has as rounded diamond shape as is shown in FIG. 3A. Also in alternative embodiments profile 64*p* can be modified by means of fitting (not shown), such as a snap in fitting, which fits into or otherwise couples with opening 64. In use, such a fitting would allow the surgeon to modify the displacement of blade 10, without having to change blades.

In other embodiments, engagement section 62 can comprise all or a portion of proximal end 61. The width 62W of the engagement section can be larger than that of other portions of proximal portion 60 so as to present more surface area for contact by drive source 20. For embodiments having slot 63, engagement section will comprise a top and bottom portion 62*t* and 62*b*. In such embodiments, top and bottom portion 62*t* and 62*b* can be configured to be independently and reciprocally engaged by drive source 20. That is each portion (62*t* and 62*b*) can reciprocate proximally and distally independent of the other portion. For example, in one embodiment during the course of one drive cycle, the drive source exerts a force to longitudinally displace for example, top portion 62*t* in a distal direction D while exerting little or no force on bottom portion 62*b*. This causes top proximal portion 60*t* to also be longitudinally displaced. During the next portion of the cycle, the drive source disengages top portion 62*t* (allowing it to reciprocate back to its original position) and now forcibly engages bottom portion 62*b* causing it to be displaced distally along with bottom 60*b*. This reciprocal motion is subsequently converted by distal portion 70 into an oscillatory movement of cutting section 72 as is discussed herein. These and related embodiments allow the cutting action of the blade to be isolated to cutting section 72 and thus eliminate or minimize injury to tissue in contact with other portions of the blade.

A discussion will now be presented of distal portion 70. As described above, distal portion 70 includes distal end 71 and a cutting section 72. Typically cutting section 72 is placed at distal end 71 but can also be placed at other location along distal portion 70. In many embodiment, cutting section 72 comprises a plurality of teeth 74, but can also comprise a single sharp edge 75 or a combination of edge and teeth (e.g. similar to a serrated knife). Teeth 74 can be hardened relative to the remainder of blade 10 to improve their ability to cut bone. Also the hardness, pitch and dimensions of teeth 74 can be selected for the particular bone tissue to be cut. The smaller teeth and pitch can be used for finer cuts in, for example, spinal tissue, whereas larger teeth and pitch can be used for cuts to the distal or proximal femur or tibia. In one embodiment, the teeth can have a finer pitch in the central portion of the blade and a coarser pitch along the outer edges of the blade. Also the teeth can be symmetrical, angled (e.g., by 45°), right angled (e.g., by 90°) as well as being arrayed on an arc line. In various embodiments, cutting section 72 and teeth 74 can be configured to cut different types of bone tissue including one or more of femoral, tibial, hip, spinal or cranial or dental mandibular or other bone tissue.

Figure 1A:
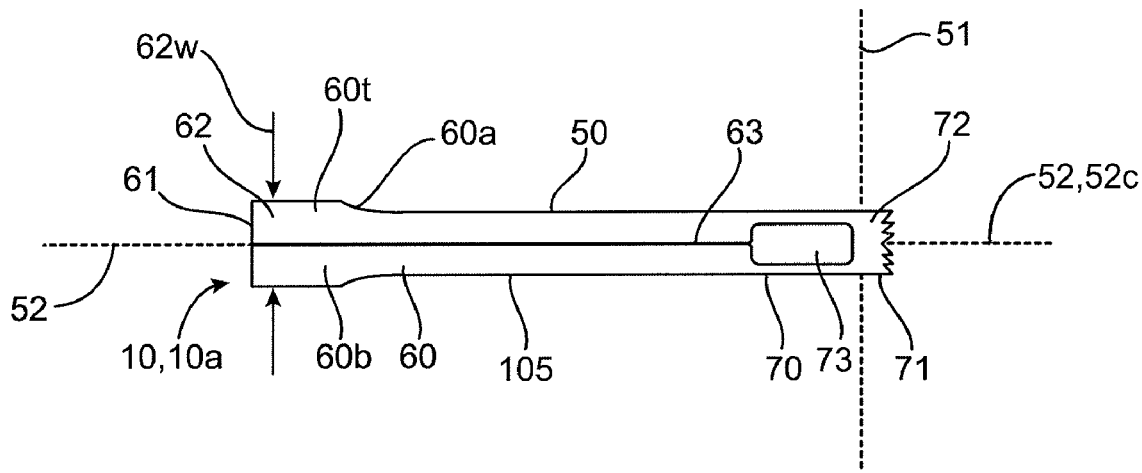
FIG. 1a is a lateral view of an embodiment of a transverse acting blade
Figure 1B:
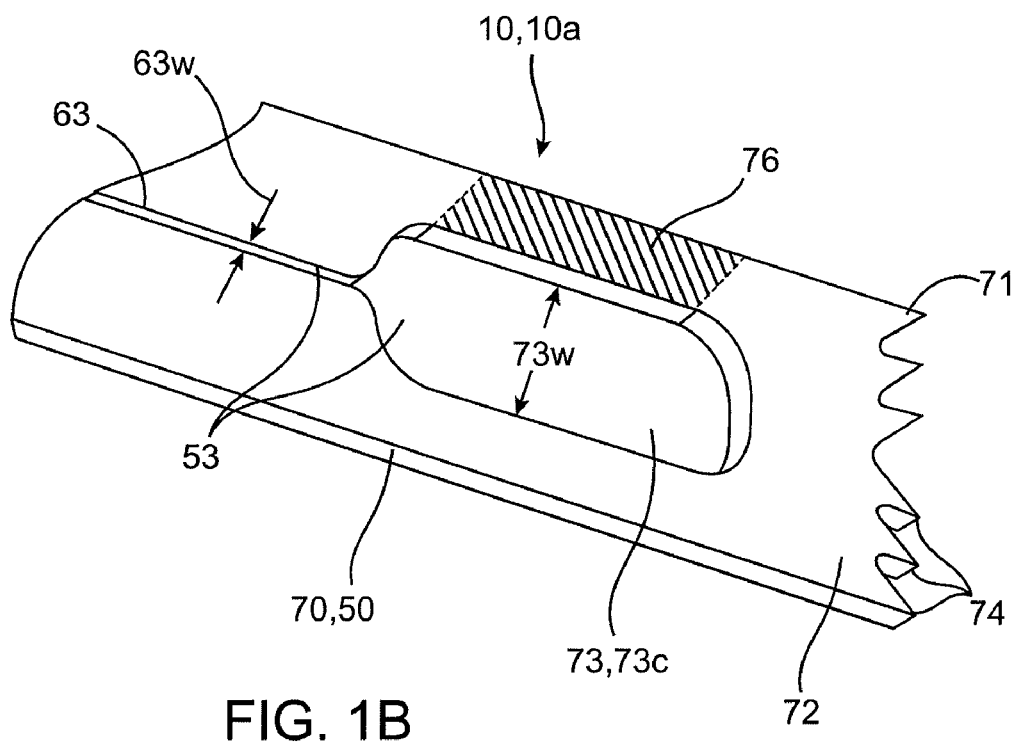
Figure 2A:
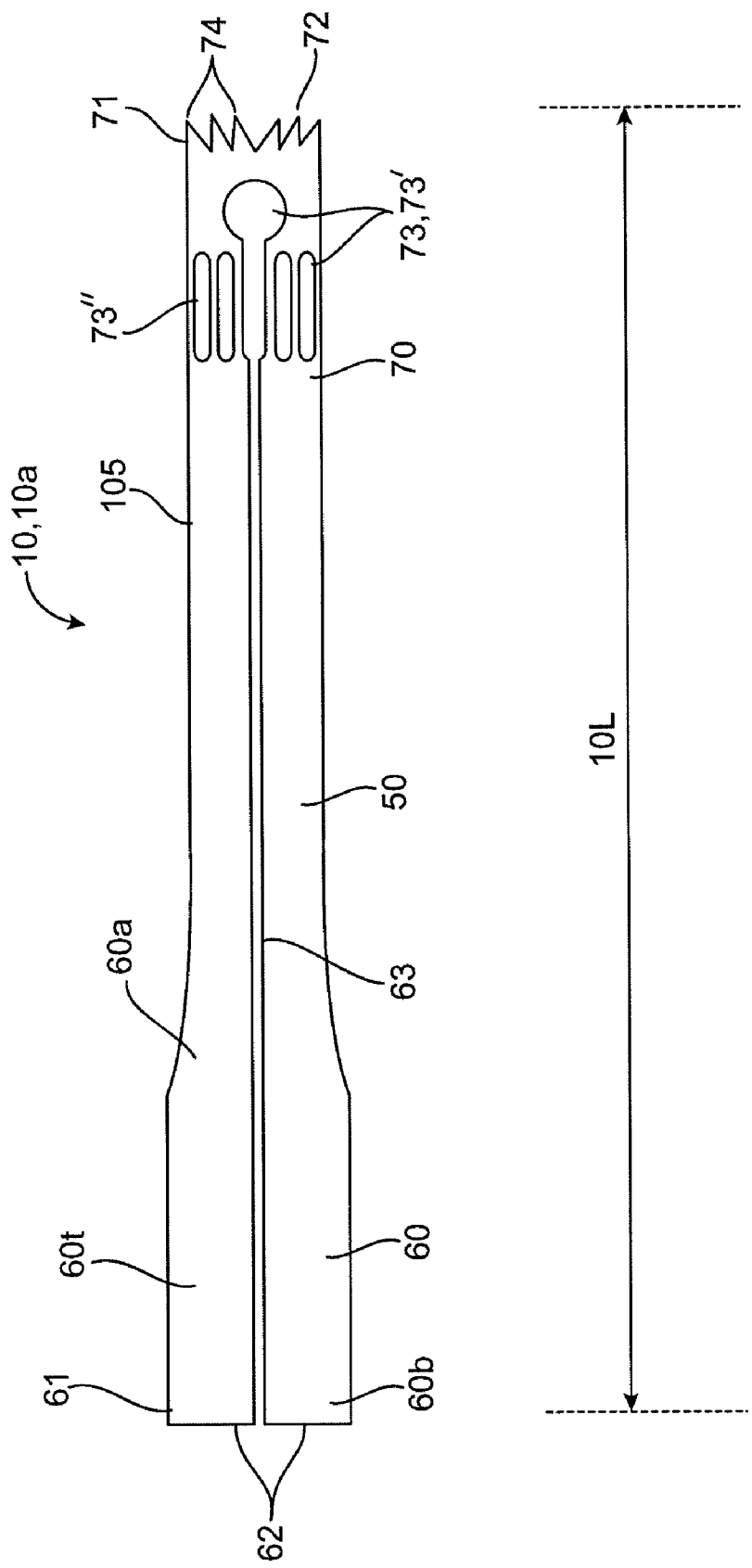
FIG. 2a is lateral view of another embodiment of a transverse acting blade.
Figure 2B:
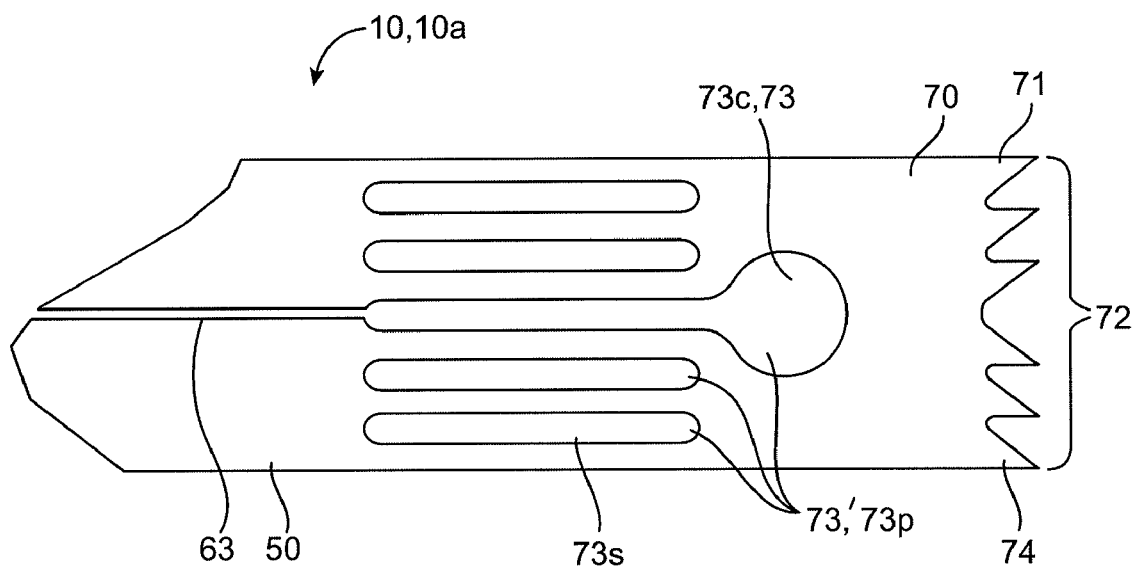

In various embodiments, distal portion 70 is configured to convert or translate longitudinal or other movement of proximal portion 60 into lateral or other movement of cutting section 72 sufficient for the cutting of bone. In many embodiments, this can be achieved by the use of one or more spaces 73 disposed within the body of the distal portion. Space 73 can have a shape and size configured to act as a pivot or motion converter 73*c* where it converts reciprocal longitudinal movement of the top and bottom portions of proximal portion 60 into lateral oscillatory movement of cutting section 72. Thus space 73 can act as one or more of a transverse motion converter and/or a reciprocal to oscillatory motion converter. Typically, space 73 will have at least a partly rounded shape and can include shapes such as circle, ellipse, oval, cassini oval or rounded rectangle and the like but also have a rectangular or other un-rounded shape. Space 73 can comprise a plurality of spaces 73' having the same or different shape arranged in a pattern 73P. In one embodiment shown in FIGS. 1*a* and 1*b*, space 73 can comprise a single space having a rounded rectangular shape wherein the space is continuous with slot 63. In another embodiment shown in FIGS. 2*a* and 2*b*, the spaces can comprise a plurality of spaces having a central space 73' surrounded by series of secondary spaces 73 which can have an elongated oval or other shape.

In preferred embodiments, space 73 has a distally tapered and/or a tapered oval shape configured to produce a substantially constant stress or constant moment arm 70*m*along the length of distal section 70 as is shown in FIG. 3*a*. These and related embodiments can be configured to produce one or more of the following: i) more control over the amount of lateral deflection of the lateral section include the cutting section; ii) reduced stress concentration in the distal section of the blade; and iii) reduced risk of shear failure of distal sections of the blade during use.

Figure 4A:
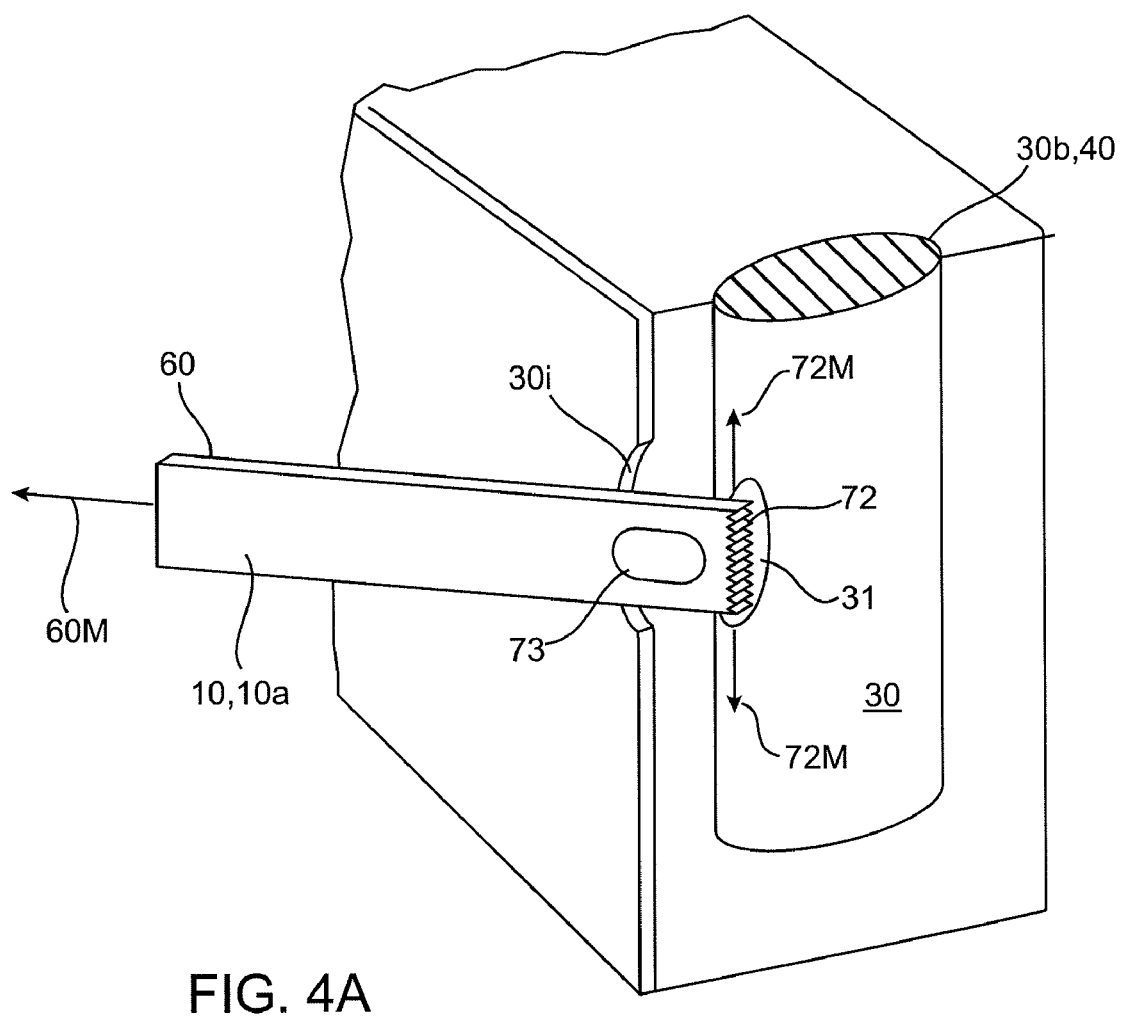
FIG. 4a is a lateral view illustrating engagement of the blade with tissue.
Figure 4B:
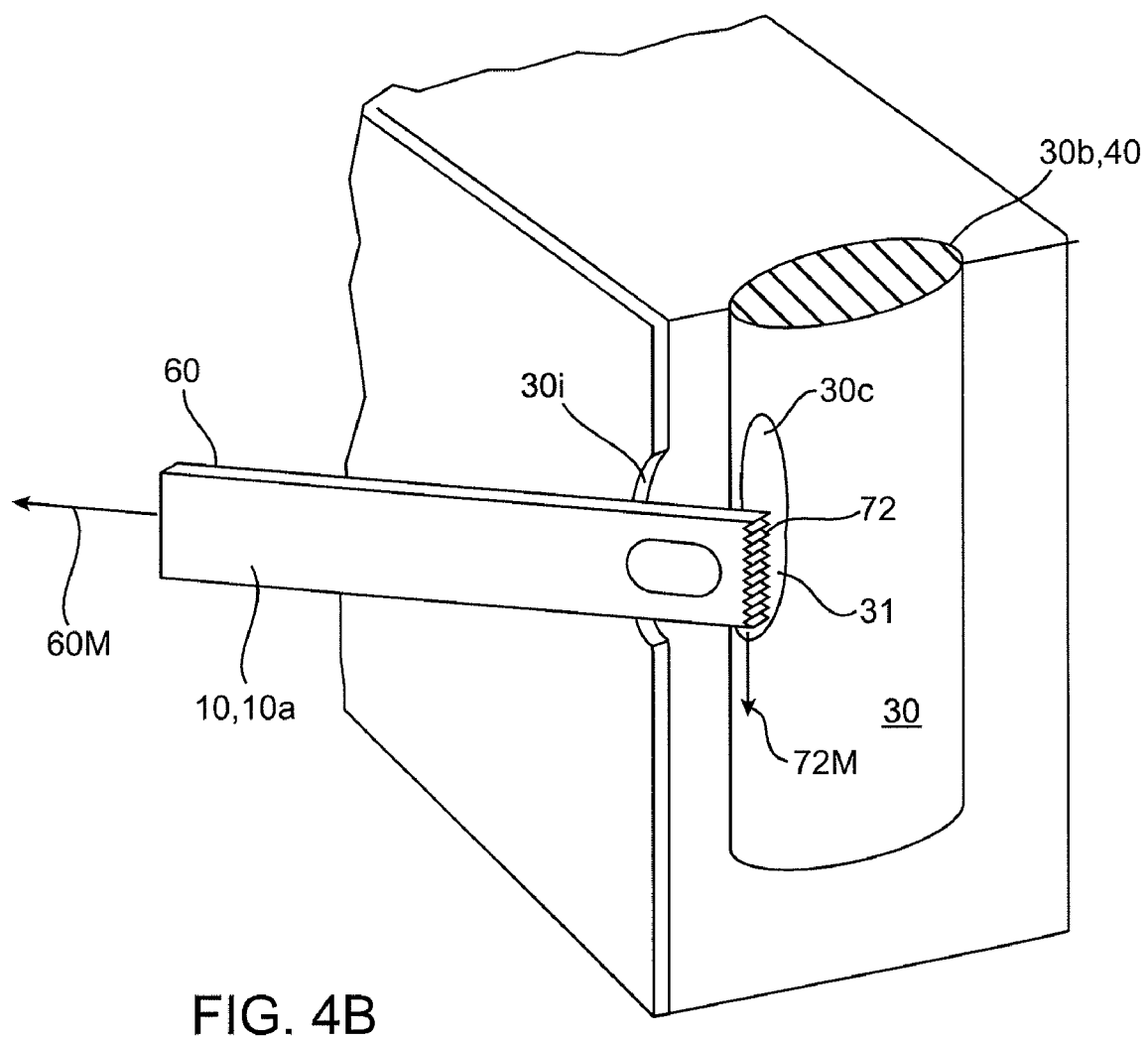
FIG. 4b is a lateral view illustrating use of the blade to make a long lateral cut in tissue

As shown in FIG. 3*b*, the longitudinal movement of the proximal section 70 is converted to lateral movement of the distal section 70. In various embodiments, the blade can be configured to produce selected amounts of lateral movement 72M of cutting section 72 with minimal or no lateral movement of the rest of the blade such that the cutting action of the blade is confined to cutting section 72. Preferably, the amount of lateral movement 72M of section 72 (as well as that of the remainder of the blade) is less than about 0.125" so as to minimize injury or disruption to surrounding tissue. In use, such minimal lateral movement allows blade 10 to be used to make long lateral cuts 30*c* in subjacent bone or other tissue with minimal injury to surrounding tissue as is shown in FIGS. 4*a* and 4*b*. Further, the lateral cuts 30*c* can be made to very deep subjacent tissue, for example six inches or deeper, without the need to retract surrounding tissue or make large incisions to get the cutting section of the blade near the target tissue site. Also, the cuts can be made in a continuous motion without the need to stop due to potential trauma to surrounding tissue. Such continuous motion results in a more uniform and faster cut. These factors allow embodiments of blade 10 to be used in a number of minimally invasive surgical procedures.

The amount of lateral movement of cutting section 72 can be controlled by several factors including the selection of the size and shape of space 73 in relation to space 63. Typically, space 73 will have larger width 73W than width 63W of space 63. The ratio between the two can be in the range of 2:1 to 10:1 or larger. In many embodiments, space 63 comprises a narrow slot and thus space 73 will have a much larger width than space 63. The ratios between the two widths can be used to control the ratio between the amount of movement between the proximal portion and the cutting portion as well as the ratio between the speeds of the two portions. Larger ratios of width 73W to width 63W will tend to produce greater amounts of movement of cutting section 72. In various embodiments, the ratio between the amount of movement (and the speed) of the proximal portion 60 and the cutting section 72 can range from 1:10, to 1:1 to 10:1. This ratio can be selected depending upon the surgical application. Smaller amounts of movement of the cutting section can be selected for procedures requiring finer cuts such as spinal and/or neurological procedures.

Typically, distal portion 70 and/or converter 73c are configured produce movement of the cutting section 72 that is substantially transverse (i.e. perpendicular) to direction of movement or proximal portion 60 as is shown in FIG. 3b. However in various embodiments, converter 73c can have a shape and size configured to produce conversion in the direction of movement of the cutting section at other angles to the movement of the proximal portions, for example, 30, 45 or 60°. In such embodiments, the cutting section 72 can itself be positioned at a non-transverse angle with respect to longitudinal axis 51. In such embodiments, converter 73c can have one of a tear like shape which can be at selected angle to longitudinal axis 51.

Blade 10 can have a shape 10s and length 10L configured for a number of surgical procedures including various orthopedic, neurological or other procedures. In various embodiments, the length 10L of the blade can be in the range of 0.5 to 10 inches, with specific embodiments of 1, 2, 3, 5 and 8 inches. The length, chemical composition, mechanical properties, and shape of the blade as well as those of the proximal and distal portions can be adapted for particular surgical procedures. As discussed above, in various embodiments, the blade can have a curve, right angle or U-shape to access various tissue sites that are recessed or directly obstructed by other tissue which can not be readily retracted. Also, the blade length as well as shape can be adapted for use in various minimally invasive and arthroscopic procedures. Accordingly, the blade can be adapted to fit through various surgical ports and conduits used in minimally invasive procedures. Particular embodiments of the blade can also be adapted to produce a very fine cutting motion of cutting section 72 with minimal and/or reduced vibration or movement of non cutting portions of the blade including proximal portion 60 and portions of distal portion 70. Such applications can include various neurological, spinal and other procedures where fine cutting action and minimal vibration is desirable so as to not exert a level of injurious force on surrounding non-target tissue. In use, such embodiments permit a surgeon to access and cut bone or other tissue that is adjacent to very delicate tissue such as nerves and vasculature including microvasculature without trauma or injury to the adjacent tissue. For example an embodiment of a transverse action low vibration blade can be used to perform various minimally invasive spinal procedures, e.g., removal of tissue or calcification such as during a laminectomy, where there is closely adjacent nerve, vascular or other sensitive tissue. In related embodiments, the cutting section of the blade can be positioned on or in an internal structure or organ such as the brain, kidney, heart or liver and a cut made with the cutting section where vibration of the remainder of the blade does not cause hemorrhage of a vascular structure of the structure or organ including a vasculature structure on the surface of the organ such as the vascular network on the surface of the brain. In various embodiments the size, shape and mechanical properties of the blade can be adapted for particular tissues sites (e.g., the brain, spine, etc) so as to allow cutting of tissue at the site while minimizing or preventing hemorrhage and other tissue trauma as described herein. This can be accomplished for example, by matching the amount of vibration and other movement of the non cutting portions of the blade to the particular tissue site.

In various embodiments, blade 10 can be fabricated from a number of or matrix of surgical grade metals, ceramics or composites known in the art. Preferably cutting section 72 including teeth 74 comprise surgical grade stainless steel material, for example, hardened and tempered stainless steel. However, these materials may be alloyed or substituted with other material, such as cera-metallic composites. When blade 10 comprises a metal, all or a portion of the blade can be fabricated using forging, machining or other metal fabrication methods known in the art. Also, the blade can be treated or processed using one or more metal treatment methods known in the art as is described herein.

Material for blade 10 can be selected based on one or more properties including elastic modulus, elastic limit, tensile strength, yield strength, compressive strength, resonance frequencies, and hardness. Selection of a resonant frequency(s) allows the blade to have sufficient lateral motion of the cutting section for cutting for a given input frequency by the drive source. It also allows the blade to be self governing such that when a threshold amount of force is applied to the blade by the surgeon, the blade becomes over-damped and cutting action of the blade is ceased.

In various embodiments, the saw blade material may be a composite. Composite include a combination of at least two materials in which one of the materials, called the reinforcing phase, is in the form of fibers, sheets, or particles, and is embedded in the other material called the matrix phase. The reinforcing material and the matrix material can be metal, ceramic, carbon-fiber, polymer, or any combination thereof to produce a saw blade that converts atraumatic, longitudinal motion along the sides of the saw blade to transverse motion of the toothed end of saw blade, allowing effective cutting and or resection of selected tissue or bone. In embodiments where the blade comprises a composite, the composite can be configured to confer to different properties (e.g. stiffness, strength, hardness, etc) to different portions of the blade. For example, the proximal portion can be configured to have greater lateral stiffness, and conversely, the distal portion more laterally flexible. Also, the cutting section and/or the engagement section can be configured to be harder and/or tougher.

Also in various embodiments, different portions of the blade may have different properties. For example cutting section 72 including teeth 74 can be fabricated from harder materials then other portion of distal portion 70 or proximal portion 60. In other embodiments different portions of the blade can have different stiffnesses. Further the difference in stiffness can be in different directions. For example, proximal portion 60 can be have a higher lateral stiffness than distal portion 70, but a lower longitudinal stiffness. Such embodiments can be configured to bias or otherwise facilitate the proximal portion to bend and flex longitudinally with minimal lateral deformation, and the distal portion to bend and flex laterally with minimal longitudinal deformation. As is discussed herein, this allows blade 10 to be used such that cutting section 72 can move laterally to cut bone tissue without trauma to tissue caused by lateral movement of proximal portion 60.

In various embodiments, one or more sections of the blade can be treated using one or more metallurgical treatments known in the art. Such treatments can include without limitation, annealing, tempering, stress relieving and work hardening. Further these and other treatments can be utilized to fabricate embodiments of the blade having portions with differences in material properties as described above. For example in one embodiment, a section 76 of distal portion 70 can be annealed or tempered to increase elasticity/flexibility and reduce brittleness. This increased elasticity can serve to have selected sections of distal portion 70 have an increased flexibility in relation to proximal portion so as to enhance the lateral movement and cutting action of cutting section 72 in response to the application of force from drive source 20 while minimizing the lateral movement of proximal portion 60. In various embodiments, tempering and annealing can be achieved using laser methods wherein the desired section is annealed or tempered by a laser beam to achieve the desired property with minimal effect to surrounding portions of the blade. Such methods allow for the precise placement of blade sections having desired material properties so as to control the amount and direction of deformation of sections of the blade in response to the application of force, for example from drive source 20. In other embodiments, laser annealing or other annealing or tempering methods can be used to produce a linear or gradual transition in material properties between sections of the blade vs. a stepped transition.

In many embodiments, blade 10 is incorporated into a saw device 25. The device can have a variety of shapes and sizes known in the surgical arts and be configured to be held in one or both hands and can also be configured to be used with a cutting guide described herein. Also blade 10 can be adapted to fit on various conventional surgical saws known in the art. Also embodiments of the invention can include a kit for doing so (e.g. an adaptor or fitting).

A discussion will now be presented of drive source 20. In various embodiments, drive source 20 can be electromechanical, pneumatic or hydraulic based. Example electro-mechanical drive sources include electric motors (AC and DC), piezoelectric systems and the like. Example electric motors include rotary DC brushless motors. Preferably, drive source 20 is configured to engage the engagement section 62 of blade 10 so as to cause reciprocating longitudinal motion of the proximal portion 60. The drive source can also be configured to induce motion of proximal portion 60 in other directions and manners.

Figure 5A:
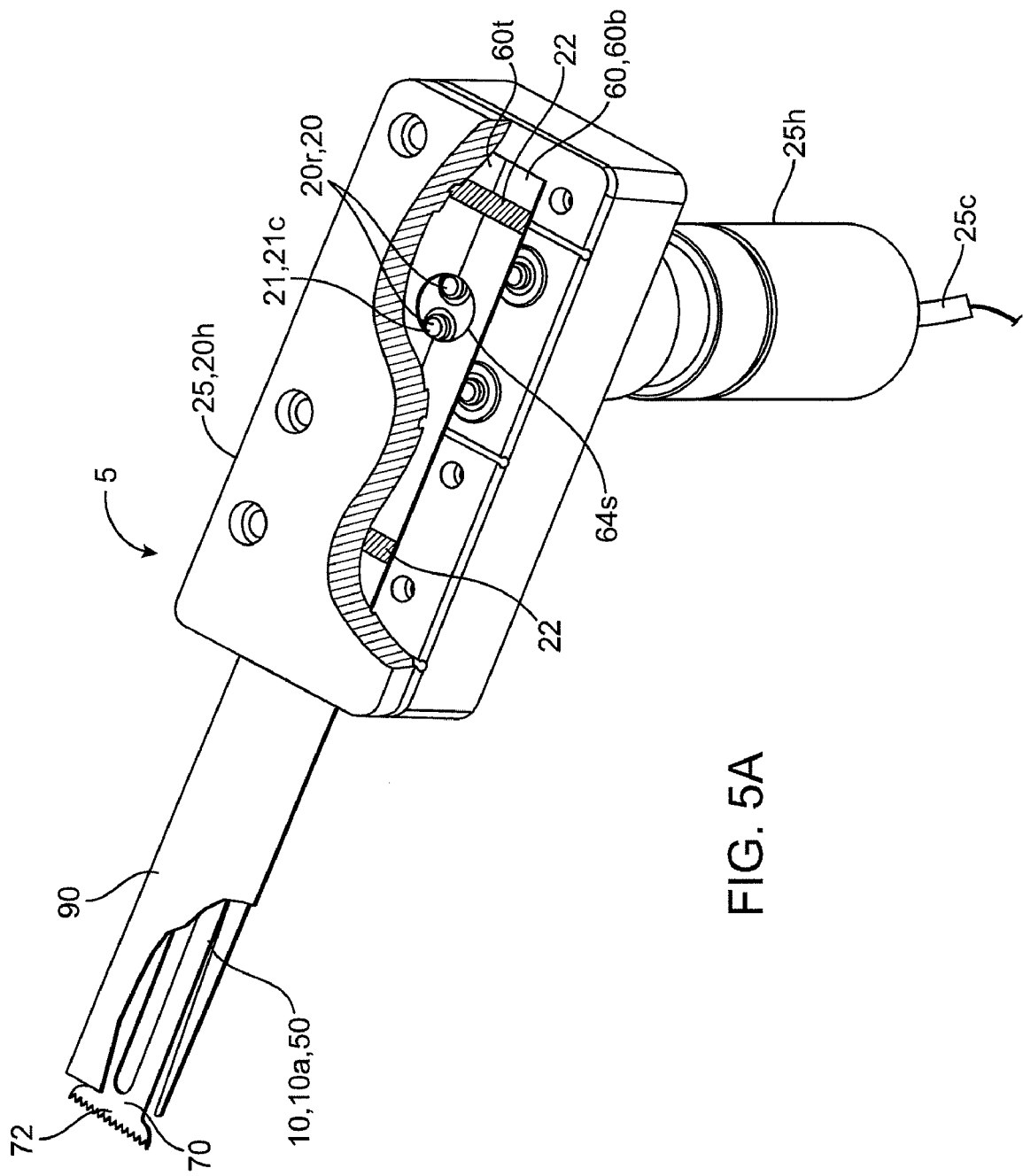
FIG. 5a is a perspective cut away view illustrating engagement of a rotary drive source with a transverse acting blade.
Figure 5B:
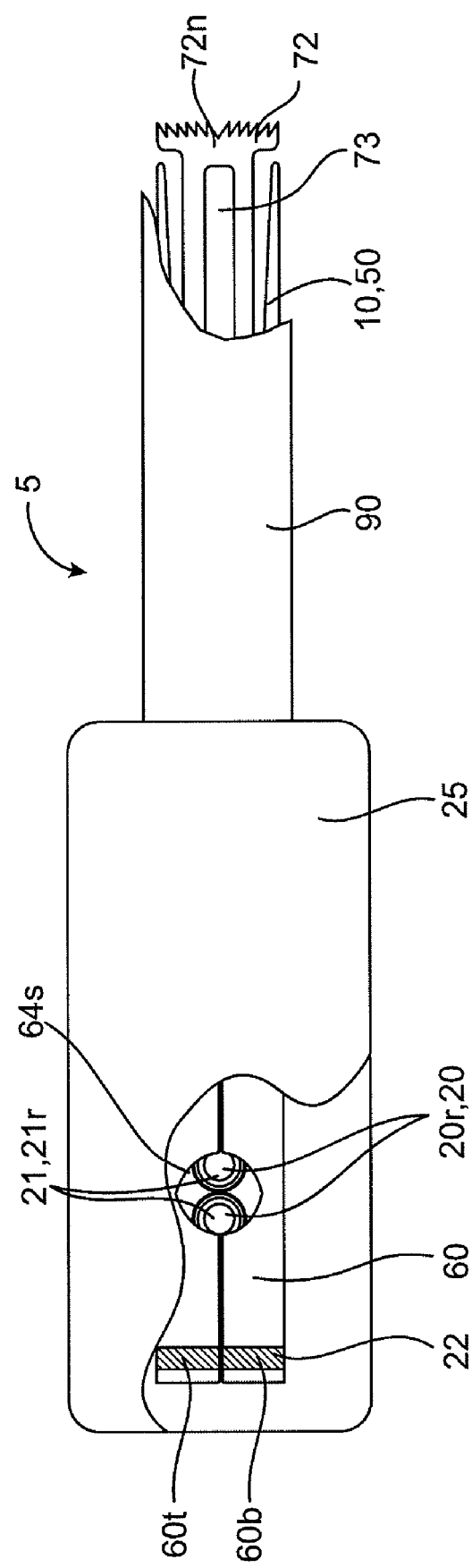
FIGS. 5b-5d are lateral views illustrating transverse movement of the blade using the rotary drive source.
Figure 5C:
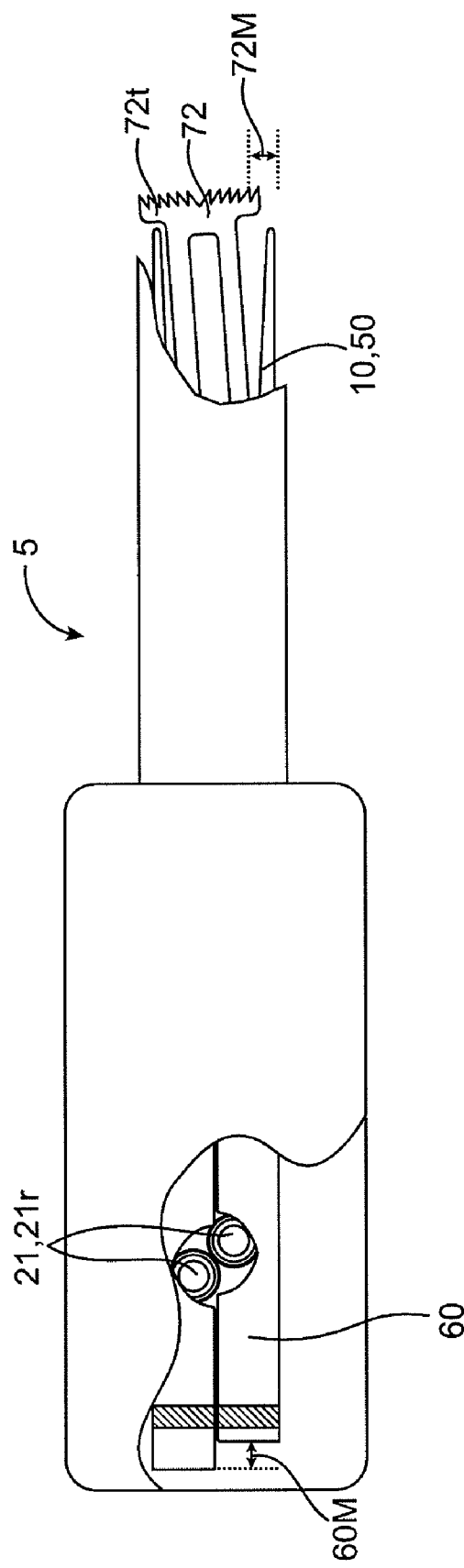
Figure 5D:
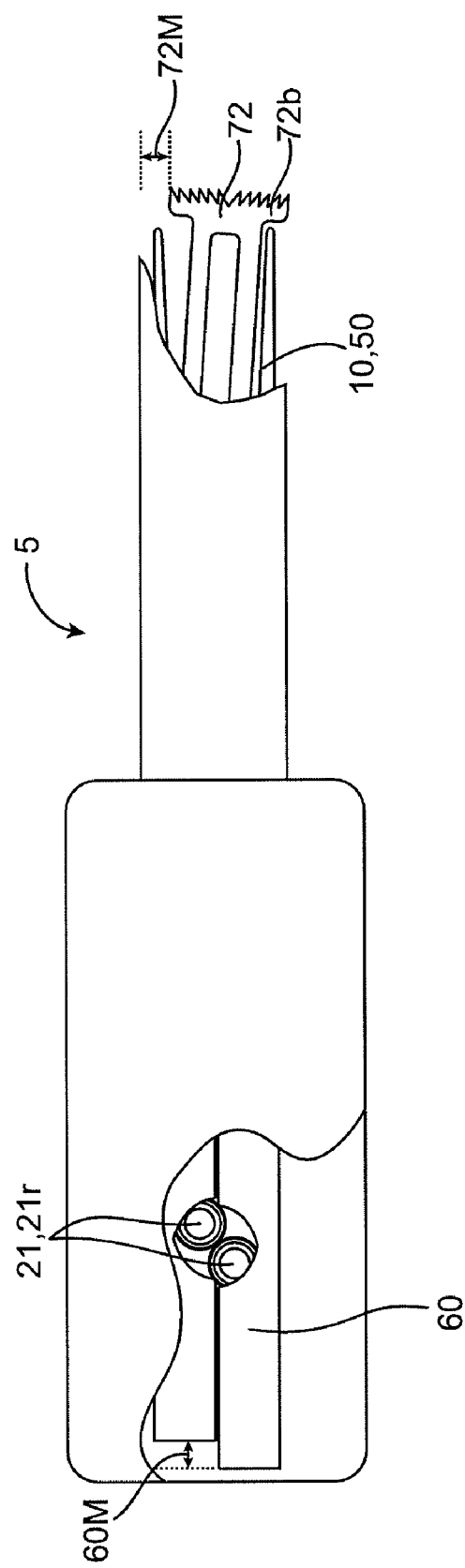

In one embodiment shown in FIGS. 5*a*-5*d*, drive source 20 can comprise a rotary mechanism 20*r* comprising two or more drive members 21 which rotate approximately 180° of phase and press against opposite halves of surfaces 64*s* so as to produce reciprocal longitudinal movement of the top and bottom proximal portions 60*t* and 60*b* of blade 10. FIGS. 5*b*-5*c* show how when drive members 21 rotate against the surface 64*s* of opening 64 they produce reciprocal longitudinal movement of proximal portions 60*t* and 60*b* so as to cause lateral oscillatory movement of cutting section 72. FIG. 5*b* shows the blade and cutting section in a neutral position 72*n*; 5*c* shows the cutting section 72 laterally displaced to a top position 72*t*; and 5*d* shows the cutting section laterally displaced to a bottom position 72*b*. In use, drive members 21 function as cams 21*c*, portions 60*t* and 60*b* as cam followers 60*f* and surface 34*s* as a cam follower surface. Mechanism 20*r* can be pneumatically powered, but is preferably electrically powered, for example, by a DC or AC motor.

Mechanism 20*r* can also include one or more guides, restraining members or dampeners 22 shown in FIG. 5*a*, which constrain movement of proximal portions of the blade to a purely longitudinal direction. For ease of discussion, members 22 will now be referred to as dampeners 22, but other forms are equally applicable. In one embodiment dampeners 22 can be a metal or plastic bands or cylinders. Dampeners 22 can constrain movement of the blade to a longitudinal direction for sections of the blade that are bounded by the guides. They can also substantially constrain movement of the blade to a single plane. Dampeners 22 can be positioned at any point along blade 10 but are preferably positioned on proximal portion 60. Also the positioning of the bands can also be used to control both the longitudinal and lateral movement of the blade. For example, greater amounts of lateral movement can be obtained by positioning the bands more proximally along the blade. In various embodiments, blade 10 can include any number of dampeners 22 but preferably, includes at least two pairs of dampeners and more preferably includes three pairs of dampeners.

In the embodiment shown in FIG. 5*a*, mechanism 20*r* can be configured to be mounted in a handheld device 20*h* which can comprise saw device 25. For ease of discussion handheld device 20*h* will now be referred to as saw device 25. For embodiments where saw device 25 is electrically powered the device can be configured to use external electrical power (AC or DC) or can be battery powered using a battery pack (e.g. lithium, nickel metal hydride, etc). Saw device 25 can include one or more connections or conduits 25C for electrical, pneumatic, or hydraulic connections both for powering drive source 20, and for light transmission, aspiration/vacuum, or the like. Connections 25C can also be configured for connection to processors internal to the device and sensors positioned on the blade 10 or elsewhere. Device 25 can also include control knobs or trigger mechanisms coupled to rheostats or other electronic device(s) or control device for controlling the speed of blade 10. The saw device 25 can also include a display (not shown) for displaying various cutting parameters such as blade speed, blade travel, applied force, and the like.

In various embodiments, device 25 and/or blade 10 separately can be configured for coupling to computer controlled robotic surgical systems. Accordingly in such embodiments connections 25C can be configured to be coupled to one or more inputs to the robotic surgical a systems to provide for connections to sensors, power systems or processors coupled to device 25 and/or blade 10. Also, the shape of device 25 and/or blade 10 can configured to be grasp or otherwise be engaged by a robotic arm or device of the robotic surgical system. Example robotic surgical systems include the da Vinci® Surgical System manufactured by Intuitive Surgical (Sunnyvale, Calif.)

Figure 6A:
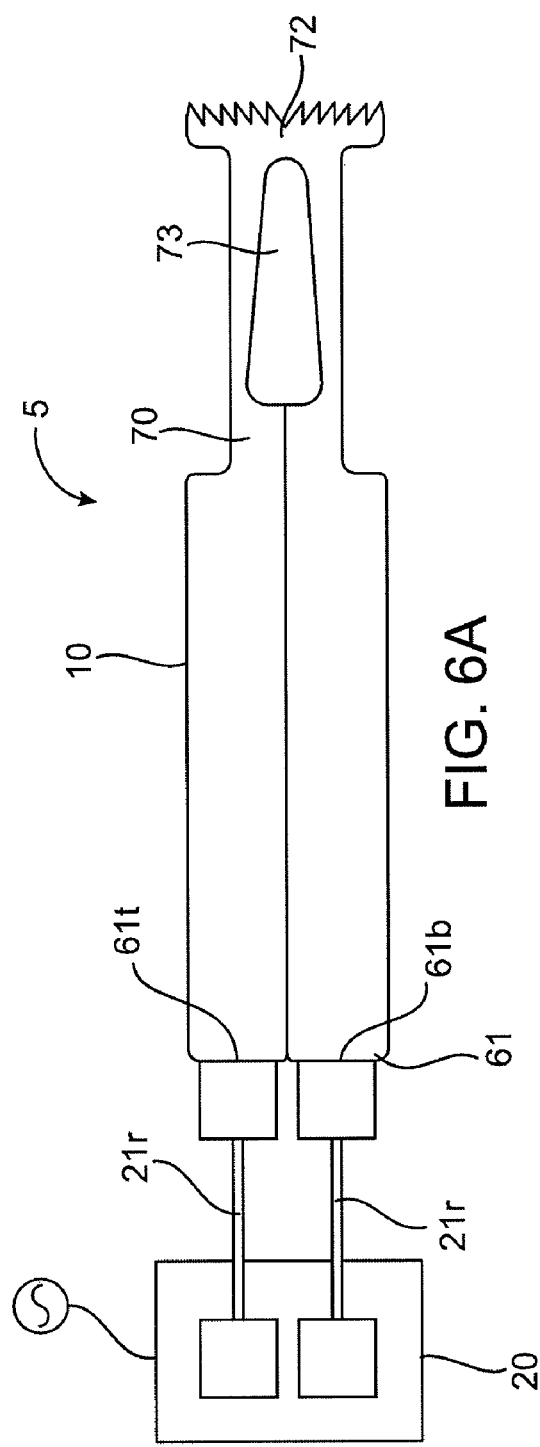
FIGS. 6a and 6b are lateral views illustrating use of another embodiment of a drive source to produce transverse movement of the blade.
Figure 6B:
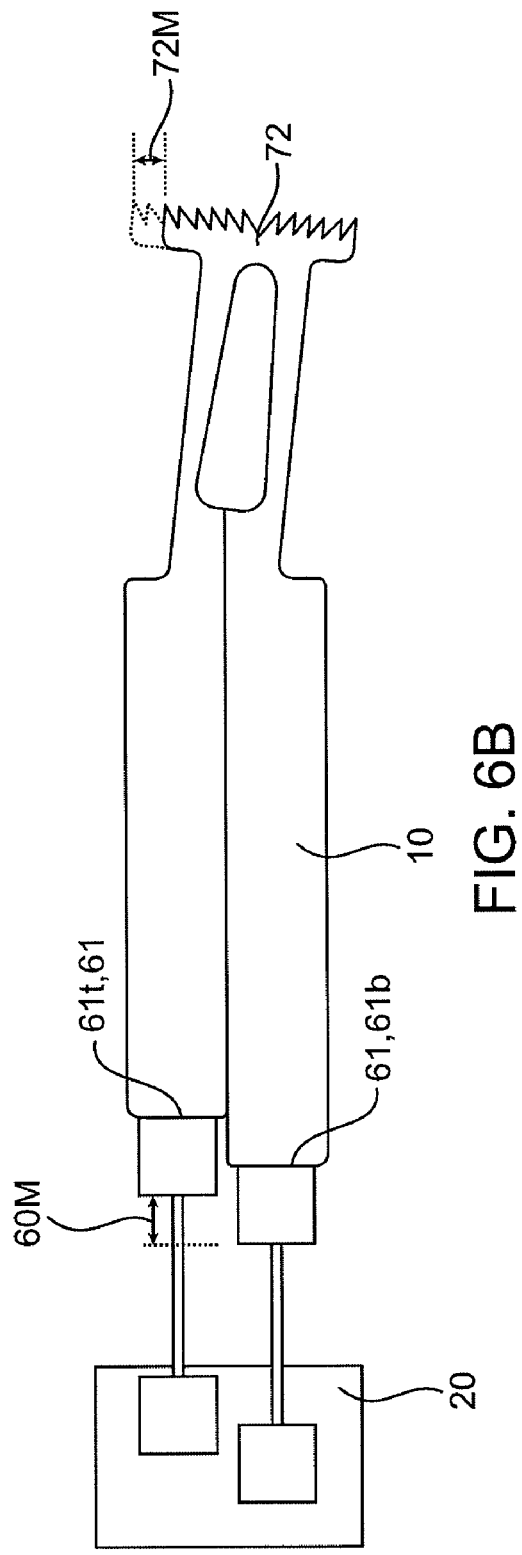

In other embodiments blade 10 can be configured to be engaged by a reciprocating drive source including an asynchronous reciprocating drive source. For example, in an embodiment shown in FIGS. 6*a* and 6*b*, the drive source can comprise two reciprocating members 21r such as cams or pistons which are configured to engage the top and bottom portions 61t and 61b of proximal end 61 that collectively comprises engagement section 62. Preferably in this and related embodiments, the reciprocating members are approximately 180° out of phase such that when one member is pushing against for example the top engagement portion 62t the other member is exerting little or no force on the bottom portion 62b. Other amounts phase angles are also contemplated. Also the drive source 20 and blade 10 can be configured to drive cutting section 72 through speeds (e.g. oscillations rates) which can range from about 50 to 1000 oscillations per second or greater.

In alternative embodiments, the drive source can comprise a voltage source and all or a portion of proximal portion 60 is fabricated from a piezo-electric material configured such that when it is energized by the voltage source it flexes or contracts causing reciprocal movement of the proximal portion which in turn is converted into lateral motion of the cutting section. In one such embodiment, the drive source can be an AC voltage source where the top and bottom portions of proximal portion 60 are configured to reciprocate back and forth in a longitudinal direction from the AC voltage. In such embodiment the speed of the reciprocation and thus the oscillation of cutting section 72 can be controlled via the frequency of the AC current.

Figure 7A:
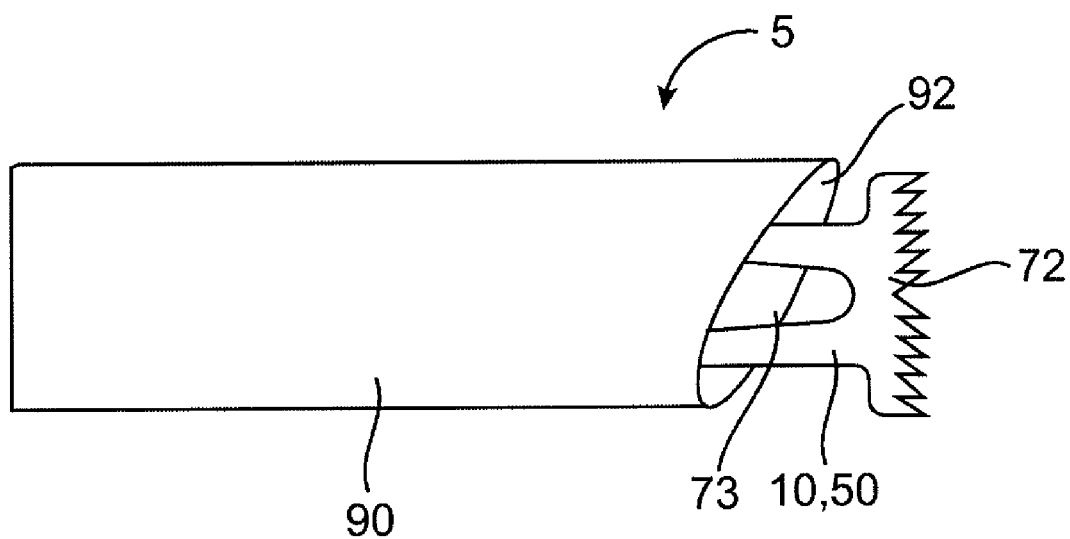
FIG. 7a is lateral view of an embodiment of the transverse acting blade having a sleeve.
Figure 7B:
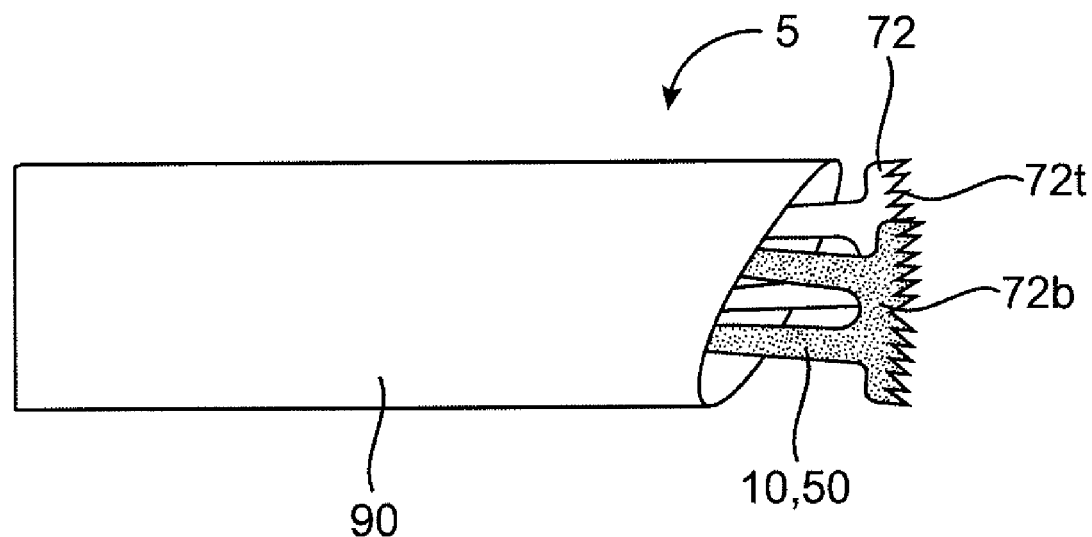
FIG. 7b is lateral view illustrating movement of a transverse acting blade within the sleeve.

Referring now to FIGS. 7a and 7b, in various embodiments, system 5 can include a sleeve 90 configured to fit over all or a portion of blade 10. Sleeve 90 can be configured to provide lateral support to blade 10 during cutting such that the blade does not bow or otherwise deform laterally during a cutting procedure or other use. Accordingly sleeve 90 has sufficient stiffness, (e.g. bending stiffness) to overcome any lateral or other force exerted by the blade on the sleeve so as to prevent or minimize any lateral deformation of the blade during use. In this and related embodiments sleeve 90 functions as a support sleeve 91. Bending stiffness can be achieved by selection of a combination of the thickness and bending modulus of the material used for the sleeve. In various embodiments all or a portion of the sleeve can be tapered so as to have a varying stiffness along a length 90l of the sleeve. Specific portions of the sleeve can thus be configured to be stiffer so as to provide greater support to selected portions of blade 10, for example those section exposed to greater amounts of stress. In this way, the sleeve can further enhance the efficiency in the conversion of motion from the proximal portion 60 to distal portion 70 to enhance the cutting action of the blade at cutting section 72 while minimizing lateral and other motion (e.g. vibrations, etc) of the proximal portion which may cause tissue cutting or other trauma. In specific embodiments, the sleeve 90 can be configured to have a selected stiffness profile 90p which can be correlated to the stress profile 10p, dimensional or other property of blade 10.

In various embodiments, the sleeve 90 can be disposed over any selected portion or length of the blade 10. In preferred embodiments, the sleeve will cover most of proximal portion 60 and a portion of distal portion 70 while leaving cutting section 72 exposed. Desirably the sleeve covers portions of the blade so as to minimize lateral movement of proximal portion 60 but allow sufficient lateral and/or other movement of distal portion 70 for cutting section 72 to effectively cut selected bone or other tissue 30. Also in various embodiments, the sleeve lumen 92 can have clearance to allow the blade to move through the sleeve. Desirably the amount of clearance is small, for example less than about 0.005". However, the clearance can be sufficient to allow the sleeve lumen to act as channel 92c for the delivery of irrigation fluid, a viewing device (e.g. a fiber optic viewing device). Also the inner lumen of the sleeve can have a lubricous coating 92 so as to minimize the amount of clearance and/or friction between the blade and the sleeve. Alternatively, the sleeve can be fixedly attached to at least a portion of the blade so as to move with the blade.

In various embodiments, sleeve 90 can be fabricated from various high strength plastics known in the art including for example, polycarbonate, polyetherimide, PEEK, acrylics and one or more thermoset plastics known in the art. Due to the stationary nature of the sleeve 90, the sleeve can have a thickness configured to fit tightly in slotted cutting guides known in the art, (e.g., cutting guides used in knee replacement surgery) without causing degradation of the dimensional integrity of the cutting guide. This allows use of cutting guides fabricated from non hardened materials such as injection molded plastic.

Figure 8:
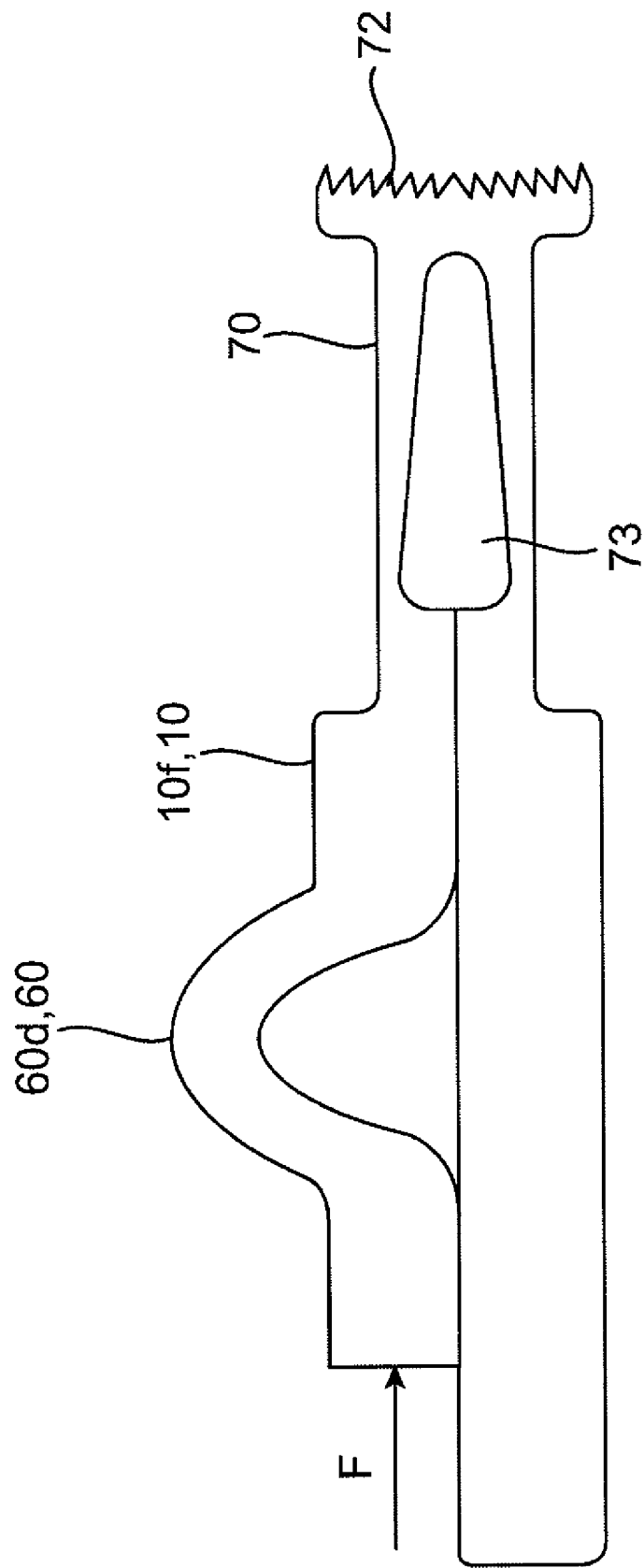
FIG. 8 is lateral view of an embodiment of the transverse acting blade having force limiting capability.
Figure 9:
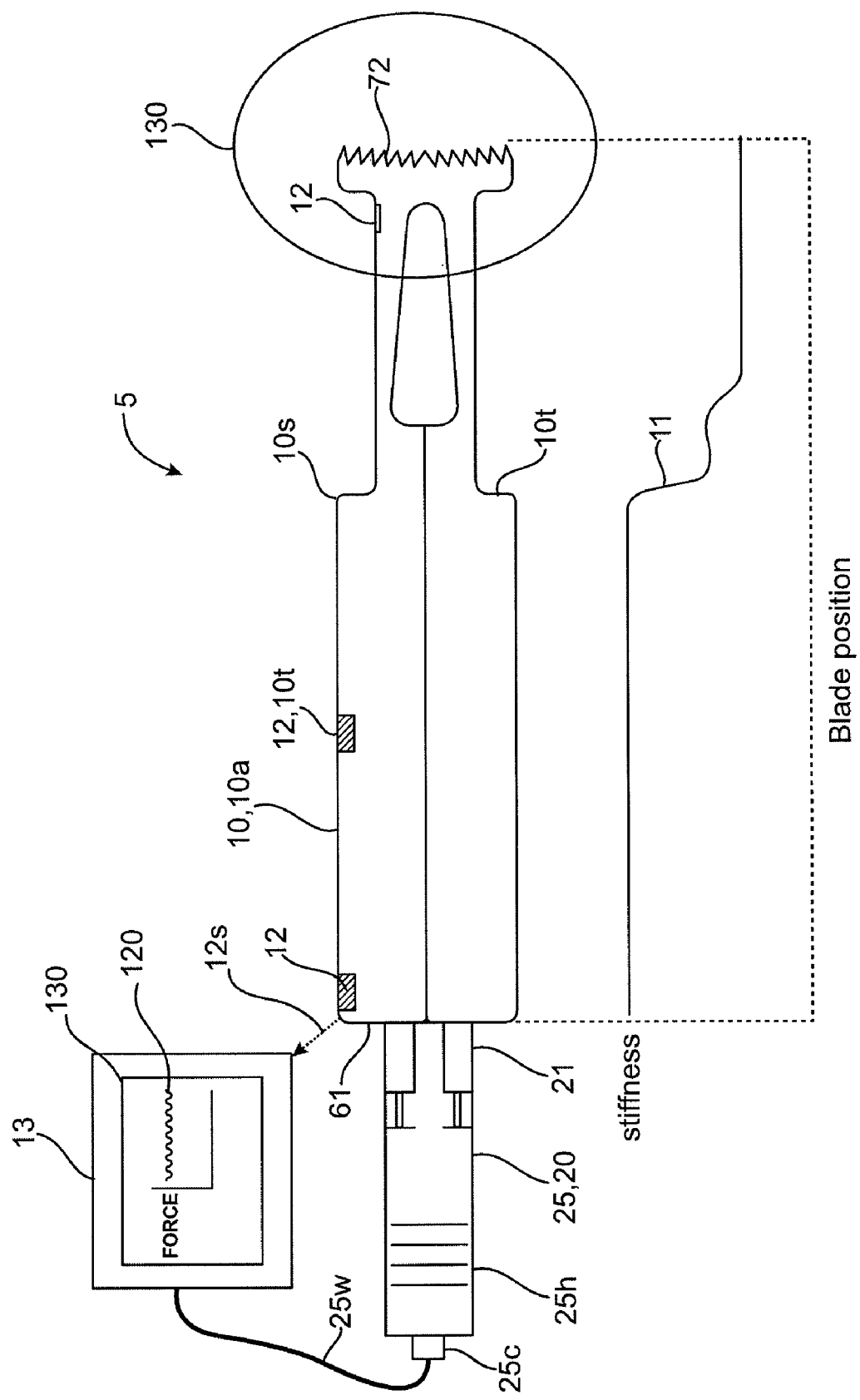
FIG. 9 is a lateral view of an embodiment of a transducing saw blade.

Sleeve 90 can be formed separately or can be formed over blade 10 using, for example, molding or extrusion methods known in the art. In one embodiment the sleeve can be coated onto the blade and then cured in place over the blade. The material for the sleeve can also be selected from materials that are compatible with one or more of EthO, gamma or e-beam or other sterilization methods known in the art. Also, the sleeve can be configured (e.g., through the selection of the material and dimensions) to allow the blade to be sterilized when the sleeve is mounted over the blade. This can be achieved through the selection of the material and dimensions of the sleeve Referring now to FIGS. 8-9, in various embodiments, blade 10 can also be configured to have various mechanical properties to allow the blade to perform one or more functions which supplement its cutting function. For example, in some embodiments, the blade can be configured to control the amount of force that the physician can apply to the blade and still have the blade cut. This can be accomplished by configuring the stiffness (e.g. column stiffness) or other mechanical properties of the blade such that when a compressive force F applied to the proximal portion 60 of the blade exceeds a threshold, the proximal portion 60 deforms (e.g., in a section 60d) so as to not transmit sufficient longitudinal force to the distal portion 70 including cutting section 72 to have the cutting section cut. In other words, the longitudinal force from the proximal section is diverted into bending the proximal portion of the blade instead of being transmitted and converted into lateral movement by the distal portion. In various embodiments, the blade can be coupled to a strain gauge (not shown) or other force monitoring device in turn coupled to a monitor/display device to let the surgeon know how much force he is applying.

In use, embodiments of the blade having a force regulating capability allow blade 10 to function as a force regulating device 10F to prevent the user from applying excessive force to the tissue site during cutting, or from progressing a cut beyond the point that force is felt by the force regulator, thus avoiding damage or trauma to tissue structures beyond the desired cutting area.

In other embodiments, blade 10 can be configured to provide the surgeon tactile or other feedback as to the amount of force applied to the blade. For example, the blade can be configured to vibrate/oscillate at the proximal end 61 in response to the amount of force applied and the cutting action of the blade. The vibrations at the proximal end are then transmitted to the handle 25h or other portion of saw device 25. In specific embodiments the amplitude and/or frequency of vibration can be lineally or otherwise correlated to the amount of applied force. In various embodiments, this can be accomplished by configuring the shape and stiffness profile 11 of the blade to transmit vibrations when a threshold amount of force is applied with increasing amounts of force resulting in an increase in the amplitude and/or frequency of the vibrations. Alternatively, the blade can be configured such that increasing amounts of force results in a decrease in the amplitude and frequency of vibrations. In one embodiment, the blade can be configured to start and then stop vibrating/oscillating over a selected range of applied pressure so as to provide the surgeon with tactile or other feedback on when he is in or out of the operational window of the proper amount of applied force. In related embodiments, a sensor 12 such as a MEMS accelerometer, MEMS pressure sensor, piezo-electric sensor or a microphone, can be coupled to the blade and in turn to a monitoring means to provide the surgeon with a quantitative indication of the amount of vibrations/oscillation/speed and in turn the amount of applied force. In various embodiments, sensors 12 can be coupled to a processor 13 including a display 13D so as to display a sensor output 120, for example applied force in graphical, numerical or other format. The blade 10 including the sensors 12 can be coupled to the display through a connection 25w or they can be configured to send a wireless signal 12s. In one embodiment, an audio output can be generated from the sensor to provide the surgeon an audio signal indicative of the applied pressure. In these and related embodiments, blade 10 acts as a transducer 10T, to provide the physician a qualitative and/or quantitative indication of the amount of force he is applying to the blade and thus to the cutting site 30. In use, such embodiments allow the surgeon to readily stay within the optimal range or window of applied force to the cutting site without the need to look away from the surgical field and/or interrupt the cutting procedure. This provides for one or more of the following: i) safer cuts because of more precise control of the applied force during the cutting process thus avoiding potential damage to adjacent tissue; ii) more precise and accurate cuts as a result of maintaining force feedback/regulation allowing the surgeon to maintain the saw blade in its most effective cutting mode. Further embodiments using force transducing blades 10T allow the surgeon to know when the blade has or is about to enter into softer tissue (e.g. cartilage, etc) because the amount of force on the blade will drop off due to the decrease in the opposing force from the progressive thinner section of uncut bone.

Figure 10:
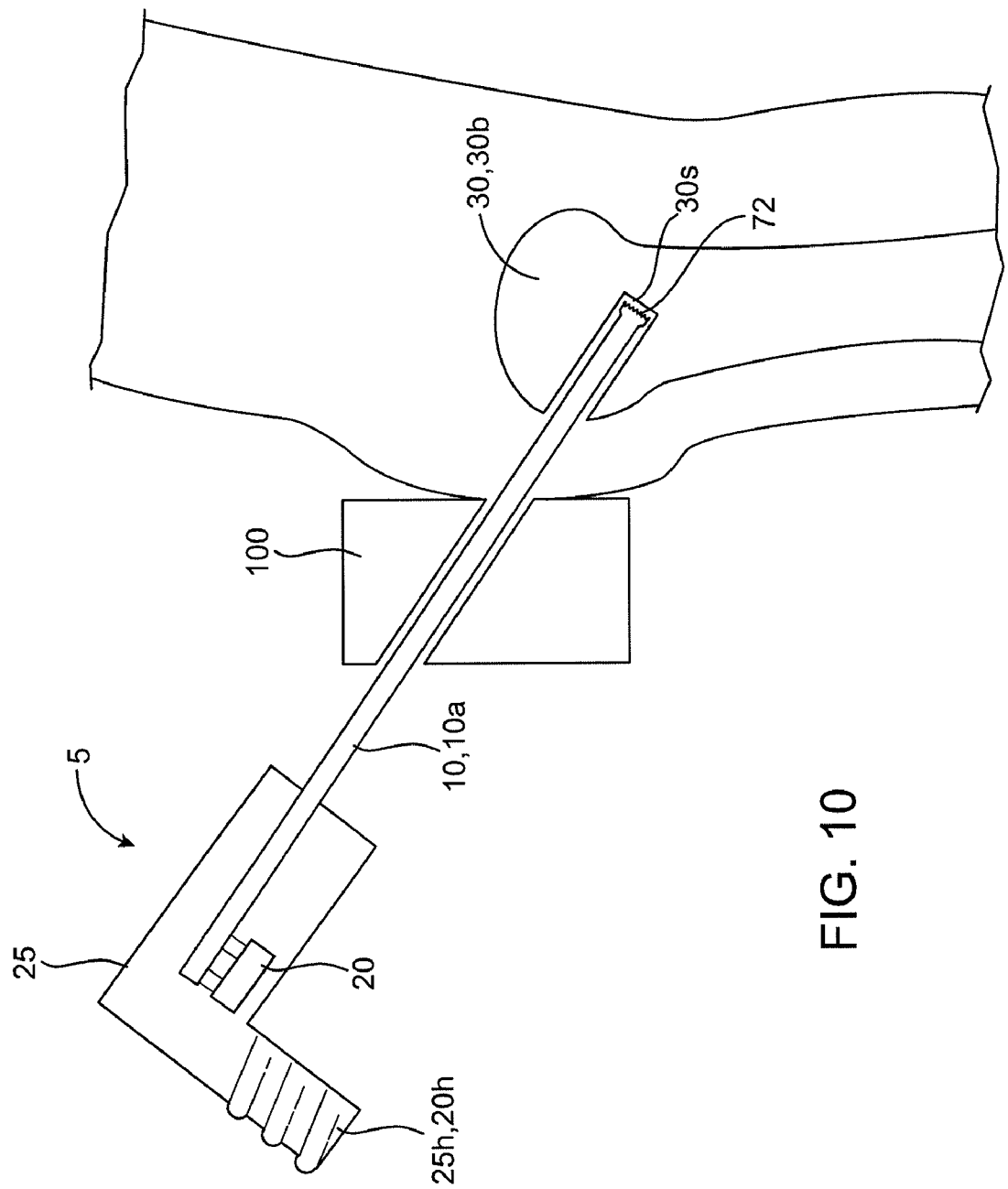
FIG. 10 is a lateral view illustrating use of a transverse acting blade with a cutting guide.

Referring now to FIG. 10, in various embodiments, system 5 can include a cutting guide 100 configured to be used with embodiments of blade 10 in making cuts in bone or other tissue. Cutting guide 100 is configured to guide blade 10 in making various angled, chamfered or other shaped cuts 30s. Further description of cutting guides is found in U.S. patent application Ser. No: 11/149,944 which is fully incorporated by reference herein.

Alternative Embodiments

A number of alterations of the blade 10 can be made to accommodate different drive sources, access different surgical sites, (e.g. the brain, spine, etc) achieve different amounts of lateral displacement of the cutting section and/or produce different blade speeds and cutting forces. These alterations can be adapted to the particular surgical application, e.g. the femur where higher amount of cutting force may desirable, vs. the brain where lower forces, lower blade speeds may be more desirable. For example the proximal portion of the blade can elongated so as to produce smaller lateral displacement of the cutting section but with higher amounts of cutting force (analogous to gear torque).

Figure 11:
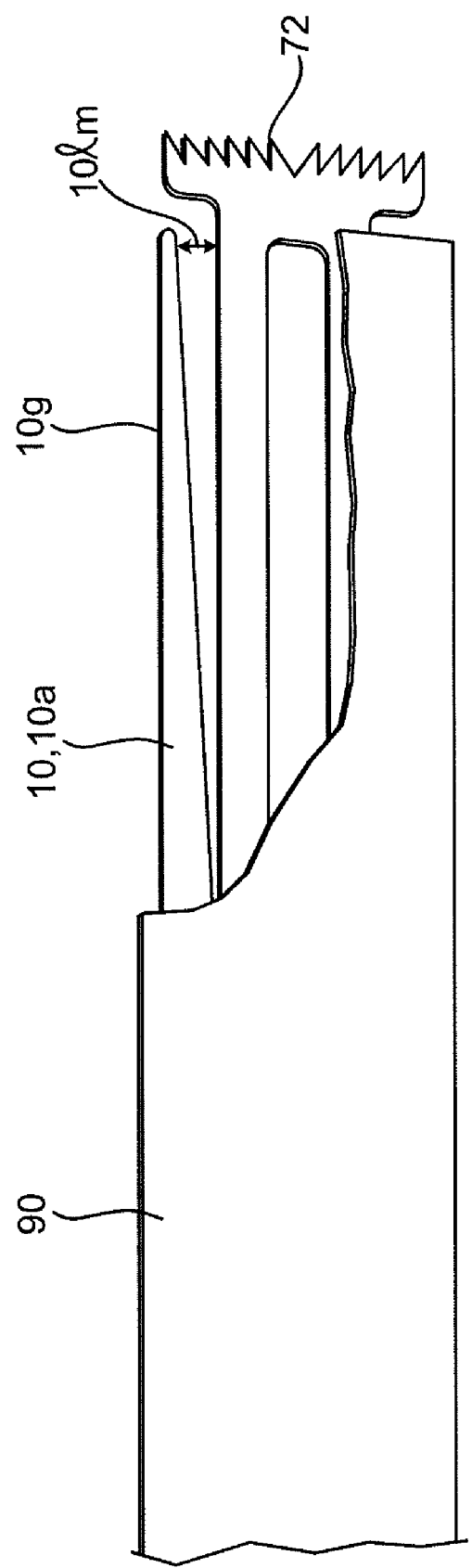
FIG. 11 is a lateral view illustrating an embodiment of the blade having a stop to limit lateral movement.

FIGS. 11-14 illustrate several alternative embodiments of blade 10 incorporating one or more of these or other alterations. FIG. 11 shows an embodiment of the blade having an integral guards or stops 15 which limits the amount of lateral movement 10lm of portions of blade 10. FIG. 5a also shows an embodiment of the blade having a stop 15. Stops 15 can extend over all or a portion of the length of blade 10. Typically, blade 10 will include a pair 15p of stops 10g so as to limit lateral movement of the blade on both sides. Alternatively, the blade can include only one stop 15 so as to limit motion on only one side of the blade. Embodiments of the blade having stops 15 can also be configured to be used with a sleeve 90 as is shown in FIG. 11. Sleeve 90 can serve to limit or dampen any vibrations that stop 15 does not. This combination provides an additional or otherwise enhanced means for limiting lateral movement and vibrations of portions of blade 10 so as to reduce the transmission of movement of vibration to surrounding tissue. In use, such embodiments serve to stabilize the blade 10 allowing the surgeon finer control over motion of the blade in various surgical procedures.

Figure 12:
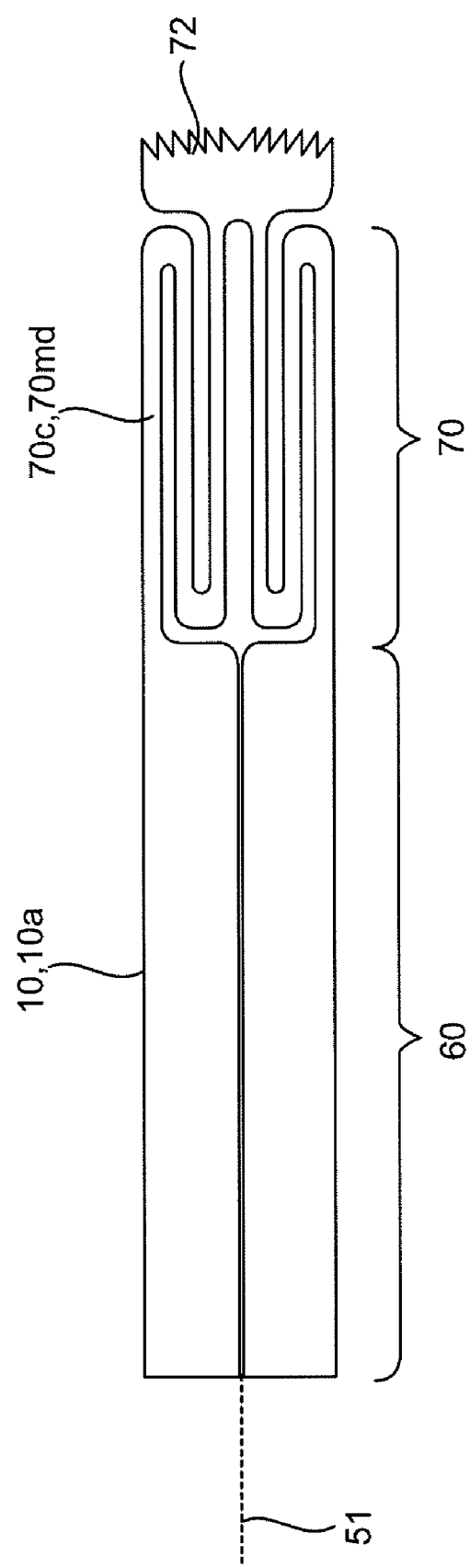
FIG. 12 is a lateral view illustrating an embodiment of the blade having a convoluted portion.
Figure 13:
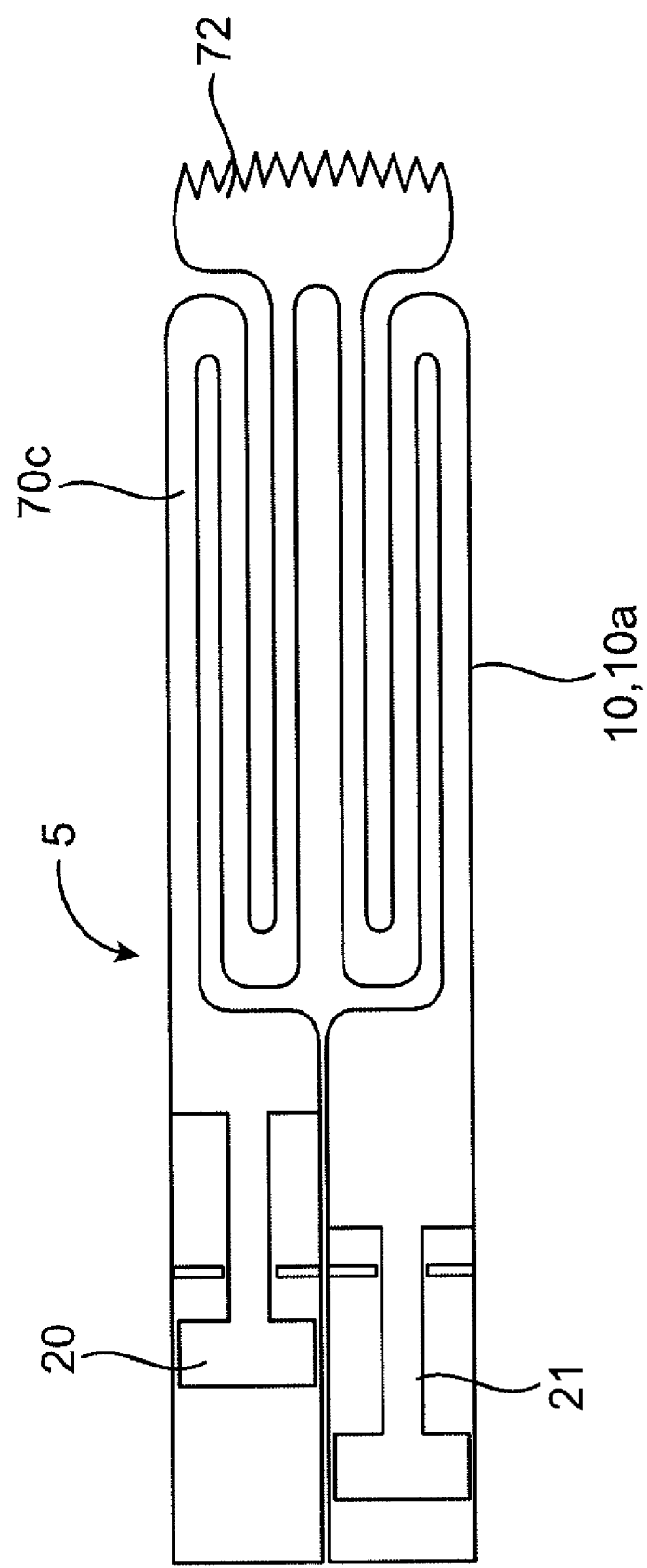
FIG. 13 is a lateral view illustrating another embodiment of the blade having a convoluted portion engaged by a drive source.

FIG. 12 shows an embodiment of blade 10 having inwardly convoluted portions 70c. Convoluted portion 70c serves to convert longitudinal movement of the proximal portion 60 to lateral movement of cutting section 72. The convoluted portions 70c also serve as a motion director 70md to control or limit any lateral movement of the distal portion 70 to an inward direction with respect longitudinal axis 51. FIG. 13 shows another embodiment of a blade having convoluted portions 70c. In this embodiment the blade is configured to be engaged by a piston or piston like drive source 20.

Figure 14:
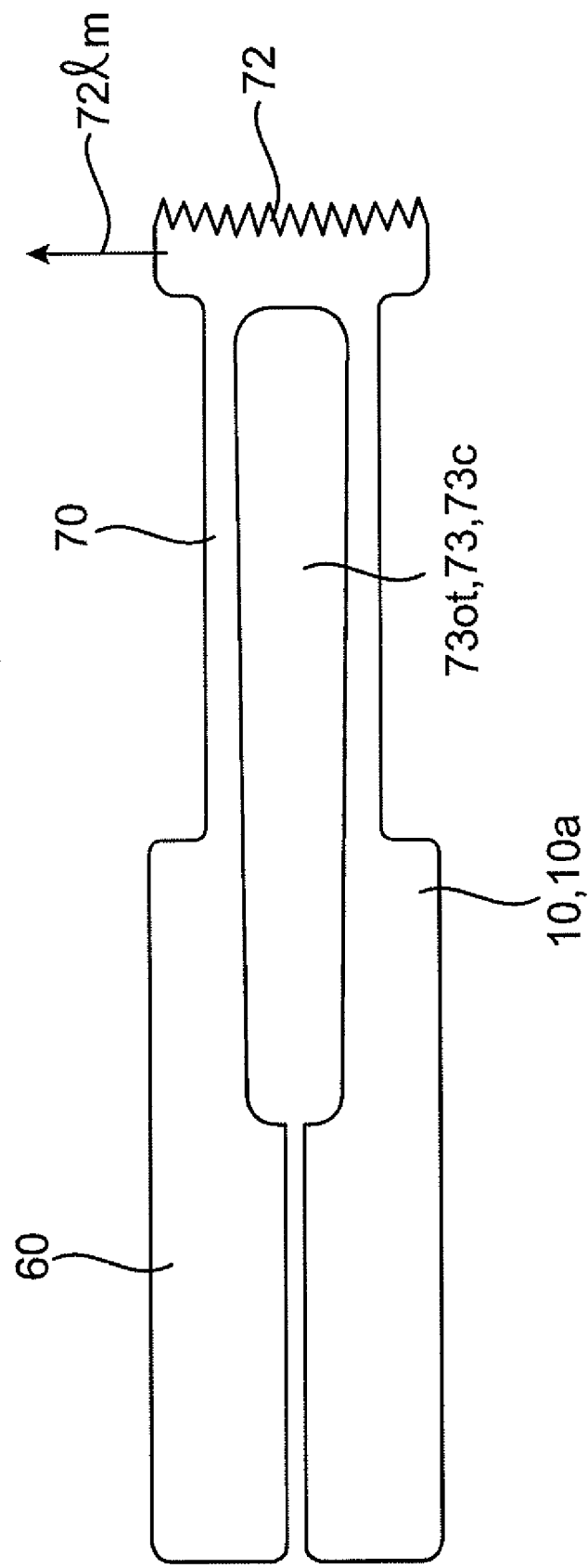
FIG. 14 is a lateral view illustrating an embodiment of the blade configured to have increased lateral movement of the cutting section.

FIG. 14 shows an embodiment of blade 10 having an outwardly tapered t space 73ot or motion converter 73c which extends in a longer direction proximally than other embodiments. The increased length and outward taper of space 73ot can be configured to produce increased amounts of lateral motion 72m of section 72. Also space 73ot can be configured to decrease the amount of force the cutting section applies to tissue. Such embodiments can be used for tissue sites having softer tissue, e.g., muscle tendons fascia, etc.

Conclusion

The foregoing description of various embodiments of the invention has been presented for purposes of illustration and description. It is not intended to limit the invention to the precise forms disclosed. Many modifications, variations and refinements will be apparent to practitioners skilled in the art. Also, the teachings of the invention have broad application in the field of surgical saws and instruments including instruments used in minimally invasive orthopedic procedures. They also have application to field of cranio-facial instruments and related procedures as well to the field of neurosurgical instruments and related procedures.

Further, elements or acts from one embodiment can be readily recombined or substituted with one or more elements or acts from other embodiments to form new embodiments. Moreover, elements that are shown or described as being combined with other elements, can in various embodiments, exists as stand alone elements. Hence, the scope of the present invention is not limited to the specifics of the exemplary embodiments, but is instead limited solely by the appended claims.

What is claimed is:

1. A saw blade for performing surgical cuts to bone tissue with minimal injury to surrounding tissue, the blade comprising:

a single piece elongated member having a first portion and a second portion having a cutting surface, wherein the first portion is engageable with a drive source to produce a longitudinal movement of the first portion, and wherein the single piece elongated member has an opening in the second portion behind the cutting surface and a slot in communication with the opening and extending from the opening to the first portion so that the first portion is split into halves which can be separately reciprocated to convert the longitudinal movement of the first portion into a lateral movement of the second portion that is sufficient to cut engaged bone tissue with the cutting surface, the movement of the first portion being substantially atraumatic to surrounding tissue and the movement of the second portion being substantially transverse to the movement of the first portion.

2. The saw blade of claim 1, wherein a portion of the blade is configured to sense a property of the blade.

3. The saw blade of claim 2, wherein the sensed property is an applied force, a vibration amplitude or a vibration frequency.

4. The saw blade of claim 1, further comprising: a sensor coupled to a portion of the blade.

5. The saw blade of claim 4, wherein the sensor includes at least one of an accelerometer, a pressure sensor, a force sensor, a MEMs sensor, a piezo-electric sensor or a microphone.

6. The saw blade of claim 1, further comprising a sleeve disposed over at least a portion of the elongated member, the sleeve configured to laterally support the blade during cutting and to be inserted into a cutting guide.

7. The saw blade of claim 1, wherein the opening increases the lateral flexibility to the second portion relative to the first portion.

8. The saw blade of claim 1, wherein the opening is configured to produce a substantially constant stress along a length of the elongated member adjacent the opening when the drive source engages the blade.

9. The saw blade of claim 1, wherein the opening is distally tapered.

10. The saw blade of claim 1, wherein the second opening is substantially oval, circular or rounded.

11. The saw blade of claim 1, wherein the second portion includes a plurality of openings.

12. The saw blade of claim 11, wherein the plurality of openings are arranged in a pattern for converting a longitudinal displacement of the first portion to a lateral displacement of the second portion.

13. The saw blade of claim 1, wherein a proximal end of the first portion is configured to engage the drive source which reciprocates the two halves.

14. The saw blade of claim 1, wherein the second portion has a lateral stiffness configured to facilitate conversion of longitudinal displacement of the first portion to lateral displacement of the second portion.

15. The saw blade of claim 14, wherein the second portion lateral stiffness is produced by annealing or tempering the second portion.

16. The saw blade of claim 14, wherein the second portion includes an annealed or tempered region.

17. The saw blade of claim 1, wherein at least a portion of the blade comprises at least one of metal, stainless steel, composite, carbon fiber composite, polymer, titanium, or ceramic.

18. The saw blade of claim 1, wherein the cutting surface includes a plurality of teeth.

19. The saw blade of claim 1, wherein the cutting surface is configured to cut at least one of femoral, tibial, humoral, spinal, cranial or mandibular tissue.

20. The saw blade of claim 1, wherein at least a portion of the blade is configured to be used with a cutting guide.

21. The saw blade of claim 1, wherein the first portion has sufficient length to allow access to bone tissue by the cutting surface up to about six inches from a skin surface.

22. The saw blade of claim 1, wherein movement of the first portion exerts a force below that necessary to sever tissue surrounding the first portion.

23. The saw blade of claim 1, wherein movement of the first portion exerts a force below that necessary to damage a vasculature or microvasculature in tissue surrounding the first portion.

24. A surgical saw system for performing surgical cuts to bone tissue with minimal injury to surrounding tissue, the system comprising:
   the saw blade of claim 1; and
   a surgical saw having a driver to separately axially reciprocate the two halves of the blade.

25. The surgical saw system of claim 24, further comprising: a cutting guide configured to guide the saw blade in cutting bone tissue.

26. The surgical saw system of claim 24, further comprising a sleeve disposed over a least a portion of the elongated member, the sleeve configured to laterally support the blade during cutting.

* * * * *